(12) United States Patent
Langeveld et al.

(10) Patent No.: US 10,345,479 B2
(45) Date of Patent: Jul. 9, 2019

(54) PORTABLE X-RAY SCANNER

(71) Applicant: Rapiscan Systems, Inc., Torrance, CA (US)

(72) Inventors: Willem Gerhardus Johannes Langeveld, Menlo Park, CA (US); Edward D. Franco, San Mateo, CA (US)

(73) Assignee: Rapiscan Systems, Inc., Torrance, CA (US)

(*) Notice: Subject to any disclaimer, the term of this patent is extended or adjusted under 35 U.S.C. 154(b) by 291 days.

(21) Appl. No.: 15/266,595

(22) Filed: Sep. 15, 2016

(65) Prior Publication Data

US 2017/0131428 A1    May 11, 2017

Related U.S. Application Data

(60) Provisional application No. 62/219,589, filed on Sep. 16, 2015.

(51) Int. Cl.
*G01N 23/04* (2018.01)
*G01V 5/00* (2006.01)

(52) U.S. Cl.
CPC .......... *G01V 5/0041* (2013.01); *G01N 23/04* (2013.01); *G01N 2223/423* (2013.01); *G01N 2223/643* (2013.01)

(58) Field of Classification Search
CPC ....... G01N 2223/423; G01N 2223/643; G01N 23/04; G01N 23/083; G01N 23/20083; G01N 23/201; G01N 2223/1016; G01N 2223/306; G01N 2223/3307; G01N 23/046; G01V 5/0041; G01V 5/005; G01V 5/0033; G01V 5/0008; G01V 5/0016; G01T 1/2985; G01T 1/1648; G01T 1/169; G01T 1/202; G01T 7/00; G01T 1/295;
(Continued)

(56) References Cited

U.S. PATENT DOCUMENTS 2,031,400 A    2/1936  Wilcox
2,299,251 A   10/1942  Perbal
(Continued)

FOREIGN PATENT DOCUMENTS

CN   1490616    4/2004
CN   1802676    7/2006
(Continued)

OTHER PUBLICATIONS

CRS Report for Congress, Aviation Security Technologies and Procedures: Screening Passengers and Baggage, Oct. 26, 2001, pp. 1-12.
(Continued)

*Primary Examiner* — Irakli Kiknadze
(74) *Attorney, Agent, or Firm* — Novel IP

(57) ABSTRACT

The present specification discloses systems for a compact and portable X-ray transmission imaging system that is used for security inspection of small items. The system includes a housing with an X-ray tunnel for receiving an article to be inspected, a conveyor for conveying the article through the tunnel, a dual source X-ray system, with a central target, for generating two overlapping cone beams, and a two-dimensional X-ray detector system for detecting the generated dual energy X-rays.

20 Claims, 9 Drawing Sheets

(58) Field of Classification Search
CPC ....... G01T 1/2008; G01T 1/24; G01T 1/2006;
G01T 1/00; G01T 1/2928; G01T 1/249;
G01T 1/1647; G01T 1/17; G01T 1/2012;
G01T 1/171; G01T 1/2018; G01T 1/242;
G01T 1/243; G01T 1/247; A61B 6/032;
A61B 6/4085; A61B 6/027; A61B 6/035;
A61B 6/4007; A61B 6/42; A61B 6/4233;
A61B 6/4291; A61B 6/4216; A61B
6/4283; A61B 6/482; H01J 43/18; H01J
2231/121; H01J 9/2272; H01J 2235/068;
H01J 2235/086; H01J 35/10
USPC .......................... 378/57, 62, 19, 9, 208, 209
See application file for complete search history.

(56) References Cited

U.S. PATENT DOCUMENTS

| | | |
|---|---|---|
| 2,636,619 A | 4/1953 | Alexander |
| 2,831,123 A | 4/1958 | Daly |
| 3,275,831 A | 9/1966 | Martin |
| 3,374,355 A | 3/1968 | Parratt |
| 3,439,166 A | 4/1969 | Chope |
| 3,707,672 A | 12/1972 | Miller |
| 3,713,156 A | 1/1973 | Pothier |
| 3,766,387 A | 10/1973 | Heffan |
| 3,784,837 A | 1/1974 | Holmstrom |
| 3,837,502 A | 9/1974 | Hornagold |
| 3,904,923 A | 9/1975 | Schwartz |
| 4,047,035 A | 9/1977 | Dennhoven |
| 4,122,783 A | 10/1978 | Pretini |
| 4,139,771 A | 2/1979 | Dennhoven |
| 4,164,138 A | 8/1979 | Burkhart |
| 4,210,811 A | 7/1980 | Dennhoven |
| 4,216,499 A | 8/1980 | Dennhoven |
| 4,239,969 A | 12/1980 | Galetta |
| 4,366,382 A | 12/1982 | Kotowski |
| 4,399,403 A | 8/1983 | Strandberg |
| 4,430,568 A | 2/1984 | Yoshida |
| 4,471,343 A | 9/1984 | Lemelson |
| 4,566,113 A | 1/1986 | Doenges |
| 4,599,740 A | 7/1986 | Cable |
| 4,641,330 A | 2/1987 | Herwig |
| 4,658,408 A | 4/1987 | Amor |
| 4,688,175 A | 8/1987 | Kaneko |
| 4,711,994 A | 12/1987 | Greenberg |
| 4,736,401 A | 4/1988 | Donges |
| 4,754,469 A | 6/1988 | Harding |
| 4,788,704 A | 11/1988 | Donges |
| 4,789,930 A | 12/1988 | Sones |
| 4,825,454 A | 4/1989 | Annis |
| 4,872,187 A | 10/1989 | Nakahata |
| 4,884,289 A | 11/1989 | Glockmann |
| 4,956,856 A | 9/1990 | Harding |
| 4,975,968 A | 12/1990 | Yukl |
| 4,979,137 A | 12/1990 | Gerstenfeld |
| 4,979,202 A | 12/1990 | Siczek |
| 4,991,189 A | 2/1991 | Boomgaarden |
| 5,007,072 A | 4/1991 | Jenkins |
| 5,008,911 A | 4/1991 | Harding |
| 5,014,293 A | 5/1991 | Boyd |
| 5,022,062 A | 6/1991 | Annis |
| 5,041,728 A | 8/1991 | Spacher |
| 5,065,418 A | 11/1991 | Bermbach |
| 5,081,456 A | 1/1992 | Michiguchi |
| 5,091,924 A | 2/1992 | Bermbach |
| 5,097,492 A | 3/1992 | Baker |
| 5,097,494 A * | 3/1992 | Pantelleria ....... G11B 15/67565 378/109 |
| 5,098,640 A | 3/1992 | Gozani |
| 5,179,581 A | 1/1993 | Annis |
| 5,181,234 A | 1/1993 | Smith |
| 5,182,764 A | 1/1993 | Peschmann |
| 5,185,778 A | 2/1993 | Magram |
| 5,197,088 A | 3/1993 | Vincent |
| 5,202,932 A | 4/1993 | Cambier |
| 5,224,144 A | 6/1993 | Annis |
| 5,227,800 A | 7/1993 | Huguenin |
| 5,237,598 A | 8/1993 | Albert |
| 5,243,693 A | 9/1993 | Maron |
| 5,247,561 A | 9/1993 | Kotowski |
| 5,253,283 A | 10/1993 | Annis |
| 5,259,012 A | 11/1993 | Baker |
| 5,260,982 A | 11/1993 | Fujii |
| 5,263,075 A | 11/1993 | McGann |
| 5,265,144 A | 11/1993 | Harding |
| 5,313,511 A | 5/1994 | Annis |
| 5,339,080 A | 8/1994 | Steinway |
| 5,345,240 A | 9/1994 | Frazier |
| 5,363,940 A | 11/1994 | Fahrion |
| 5,367,552 A | 11/1994 | Peschmann |
| 5,379,334 A | 1/1995 | Zimmer |
| 5,420,905 A | 5/1995 | Bertozzi |
| 5,490,218 A | 2/1996 | Krug |
| 5,493,596 A | 2/1996 | Annis |
| 5,503,424 A | 4/1996 | Agopian |
| 5,524,133 A | 6/1996 | Neale |
| 5,552,705 A | 9/1996 | Keller |
| 5,557,283 A | 9/1996 | Sheen |
| 5,590,057 A | 12/1996 | Fletcher |
| 5,600,303 A | 2/1997 | Husseiny |
| 5,600,700 A | 2/1997 | Krug |
| 5,606,167 A | 2/1997 | Miller |
| 5,638,420 A | 6/1997 | Armistead |
| 5,642,393 A | 6/1997 | Krug |
| 5,642,394 A | 6/1997 | Rothschild |
| 5,654,555 A | 8/1997 | Buytaert |
| 5,660,549 A | 8/1997 | Witt |
| 5,666,393 A | 9/1997 | Annis |
| 5,687,210 A | 11/1997 | Maitrejean |
| 5,689,239 A | 11/1997 | Turner |
| 5,692,028 A | 11/1997 | Geus |
| 5,692,029 A | 11/1997 | Husseiny |
| 5,699,400 A | 12/1997 | Lee |
| 5,745,543 A | 4/1998 | De |
| 5,751,837 A | 5/1998 | Watanabe |
| 5,764,683 A | 6/1998 | Swift |
| 5,768,334 A | 6/1998 | Maitrejean |
| 5,787,145 A | 7/1998 | Geus |
| 5,805,660 A | 9/1998 | Perion |
| 5,835,558 A | 11/1998 | Maschke |
| 5,838,758 A | 11/1998 | Krug |
| 5,838,759 A | 11/1998 | Armistead |
| 5,842,578 A | 12/1998 | Cordeiro |
| 5,875,226 A | 2/1999 | Yokouchi |
| 5,882,206 A | 3/1999 | Gillio |
| 5,903,623 A | 5/1999 | Swift |
| 5,909,478 A | 6/1999 | Polichar |
| 5,910,973 A | 6/1999 | Grodzins |
| 5,930,326 A | 7/1999 | Rothschild |
| 5,940,468 A | 8/1999 | Huang |
| 5,970,113 A | 10/1999 | Crawford |
| 5,974,111 A | 10/1999 | Krug |
| 6,026,135 A | 2/2000 | McFee |
| 6,031,890 A | 2/2000 | Bermbach |
| 6,044,353 A | 3/2000 | Pugliese |
| 6,054,712 A | 4/2000 | Komardin |
| 6,056,671 A | 5/2000 | Marmer |
| 6,058,158 A | 5/2000 | Eiler |
| 6,058,159 A | 5/2000 | Conway |
| 6,067,344 A | 5/2000 | Grodzins |
| 6,081,580 A | 6/2000 | Grodzins |
| 6,088,423 A | 7/2000 | Krug |
| 6,094,472 A | 7/2000 | Smith |
| 6,118,850 A | 9/2000 | Mayo |
| 6,128,365 A | 10/2000 | Bechwati |
| 6,137,895 A | 10/2000 | Al-Sheikh |
| 6,151,381 A | 11/2000 | Grodzins |
| 6,172,712 B1 | 1/2001 | Beard |
| 6,184,841 B1 | 2/2001 | Shober |
| 6,188,743 B1 | 2/2001 | Tybinkowski |
| 6,188,747 B1 | 2/2001 | Geus |
| 6,192,101 B1 | 2/2001 | Grodzins |
| 6,192,104 B1 | 2/2001 | Adams |

(56) References Cited

U.S. PATENT DOCUMENTS

| | | |
|---|---|---|
| 6,195,413 B1 | 2/2001 | Geus |
| 6,198,795 B1 | 3/2001 | Naumann |
| 6,216,540 B1 | 4/2001 | Nelson |
| 6,218,943 B1 | 4/2001 | Ellenbogen |
| 6,220,099 B1 | 4/2001 | Marti |
| 6,236,709 B1 | 5/2001 | Perry |
| 6,249,567 B1 | 6/2001 | Rothschild |
| 6,252,929 B1 | 6/2001 | Swift |
| 6,256,369 B1 | 7/2001 | Lai |
| 6,278,115 B1 | 8/2001 | Annis |
| 6,282,260 B1 | 8/2001 | Grodzins |
| 6,288,676 B1 | 9/2001 | Maloney |
| 6,292,533 B1 | 9/2001 | Swift |
| 6,301,326 B2 | 10/2001 | Bjorkholm |
| 6,301,327 B1 | 10/2001 | Martens |
| 6,304,627 B1 | 10/2001 | Horbaschek |
| 6,304,629 B1 | 10/2001 | Conway |
| 6,315,308 B1 | 11/2001 | Konopka |
| 6,320,933 B1 | 11/2001 | Grodzins |
| 6,342,696 B1 | 1/2002 | Chadwick |
| 6,347,132 B1 | 2/2002 | Annis |
| 6,356,620 B1 | 3/2002 | Rothschild |
| 6,359,582 B1 | 3/2002 | MacAleese |
| 6,359,597 B2 | 3/2002 | Haj-Yousef |
| 6,370,222 B1 | 4/2002 | Cornick |
| 6,417,797 B1 | 7/2002 | Cousins |
| 6,418,194 B1 | 7/2002 | McPherson |
| 6,421,420 B1 | 7/2002 | Grodzins |
| 6,424,695 B1 | 7/2002 | Grodzins |
| 6,430,255 B2 | 8/2002 | Fenkart |
| 6,434,219 B1 | 8/2002 | Rothschild |
| 6,435,715 B1 | 8/2002 | Betz |
| 6,442,233 B1 | 8/2002 | Grodzins |
| 6,445,765 B1 | 9/2002 | Frank |
| 6,453,003 B1 | 9/2002 | Springer |
| 6,453,007 B2 | 9/2002 | Adams |
| 6,456,093 B1 | 9/2002 | Merkel |
| 6,456,684 B1 | 9/2002 | Mun |
| 6,459,755 B1 | 10/2002 | Li |
| 6,459,761 B1 | 10/2002 | Grodzins |
| 6,459,764 B1 | 10/2002 | Chalmers |
| 6,469,624 B1 | 10/2002 | Whan |
| 6,473,487 B1 | 10/2002 | Le |
| RE37,899 E | 11/2002 | Grodzins |
| 6,480,141 B1 | 11/2002 | Toth |
| 6,483,894 B2 | 11/2002 | Hartick |
| 6,501,414 B2 | 12/2002 | Arndt |
| 6,507,025 B1 | 1/2003 | Verbinski |
| 6,507,278 B1 | 1/2003 | Brunetti |
| 6,532,276 B1 | 3/2003 | Hartick |
| 6,542,574 B2 | 4/2003 | Grodzins |
| 6,542,578 B2 | 4/2003 | Ries |
| 6,542,580 B1 | 4/2003 | Carver |
| 6,543,599 B2 | 4/2003 | Jasinetzky |
| 6,546,072 B1 | 4/2003 | Chalmers |
| 6,552,346 B2 | 4/2003 | Verbinski |
| 6,563,903 B2 | 5/2003 | Kang |
| 6,567,496 B1 | 5/2003 | Sychev |
| 6,580,778 B2 | 6/2003 | Meder |
| 6,584,170 B2 | 6/2003 | Aust |
| 6,597,760 B2 | 7/2003 | Beneke |
| 6,606,516 B2 | 8/2003 | Levine |
| 6,614,872 B2 | 9/2003 | Bueno |
| 6,621,888 B2 | 9/2003 | Grodzins |
| 6,628,745 B1 | 9/2003 | Annis |
| 6,634,668 B2 | 10/2003 | Urffer |
| 6,636,581 B2 | 10/2003 | Sorenson |
| 6,650,276 B1 | 11/2003 | Lawless |
| 6,653,588 B1 | 11/2003 | Gillard-Hickman |
| 6,658,087 B2 | 12/2003 | Chalmers |
| 6,663,280 B2 | 12/2003 | Doenges |
| 6,665,373 B1 | 12/2003 | Kotowski |
| 6,665,433 B2 | 12/2003 | Roder |
| 6,674,367 B2 | 1/2004 | Sweatte |
| 6,702,459 B2 | 3/2004 | Barnes |
| 6,707,879 B2 | 3/2004 | McClelland |
| 6,713,773 B1 | 3/2004 | Lyons |
| 6,721,391 B2 | 4/2004 | McClelland |
| 6,735,477 B2 | 5/2004 | Levine |
| 6,749,207 B2 | 6/2004 | Nadeau |
| 6,763,635 B1 | 7/2004 | Lowman |
| 6,765,527 B2 | 7/2004 | Jablonski |
| 6,768,317 B2 | 7/2004 | Moeller |
| 6,785,357 B2 | 8/2004 | Bernardi |
| 6,796,944 B2 | 9/2004 | Hall |
| 6,798,863 B2 | 9/2004 | Sato |
| 6,812,426 B1 | 11/2004 | Kotowski |
| 6,816,571 B2 | 11/2004 | Bijjani |
| 6,823,039 B2 | 11/2004 | Hoheisel |
| 6,831,590 B1 | 12/2004 | Steinway |
| 6,837,422 B1 | 1/2005 | Meder |
| 6,839,403 B1 | 1/2005 | Kotowski |
| 6,843,599 B2 | 1/2005 | Le |
| 6,856,271 B1 | 2/2005 | Hausner |
| 6,856,667 B2 | 2/2005 | Ellenbogen |
| 6,876,322 B2 | 4/2005 | Keller |
| 6,891,381 B2 | 5/2005 | Bailey |
| 6,894,636 B2 | 5/2005 | Anderton |
| 6,899,540 B1 | 5/2005 | Neiderman |
| 6,901,346 B2 | 5/2005 | Tracy |
| 6,920,197 B2 | 7/2005 | Kang |
| 6,922,460 B2 | 7/2005 | Skatter |
| 6,924,487 B2 | 8/2005 | Bolozdynya |
| 6,928,141 B2 | 8/2005 | Carver |
| 6,952,163 B2 | 10/2005 | Huey |
| 6,988,610 B2 | 1/2006 | Fromme |
| 7,012,256 B1 | 3/2006 | Roos |
| 7,039,159 B2 | 5/2006 | Muenchau |
| 7,046,768 B1 | 5/2006 | Gilevich |
| 7,072,434 B1 | 7/2006 | Tybinkowski |
| 7,092,485 B2 | 8/2006 | Kravis |
| 7,106,830 B2 | 9/2006 | Rosner |
| 7,110,925 B2 | 9/2006 | Pendergraft |
| 7,151,447 B1 | 12/2006 | Willms |
| 7,151,817 B1 | 12/2006 | Abraham |
| 7,164,747 B2 | 1/2007 | Ellenbogen |
| 7,193,515 B1 | 3/2007 | Roberts |
| 7,203,276 B2 | 4/2007 | Arsenault |
| 7,207,713 B2 | 4/2007 | Lowman |
| 7,215,738 B2 | 5/2007 | Muenchau |
| 7,257,189 B2 | 8/2007 | Modica |
| 7,286,634 B2 | 10/2007 | Sommer |
| 7,317,390 B2 | 1/2008 | Huey |
| 7,322,745 B2 | 1/2008 | Agrawal |
| 7,356,115 B2 | 4/2008 | Ford |
| 7,366,281 B2 | 4/2008 | Skatter |
| 7,366,282 B2 | 4/2008 | Peschmann |
| 7,369,643 B2 | 5/2008 | Kotowski |
| 7,379,530 B2 | 5/2008 | Hoff |
| 7,395,563 B2 | 7/2008 | Whitmore |
| 7,397,891 B2 | 7/2008 | Johnson |
| 7,400,701 B1 | 7/2008 | Cason |
| 7,417,440 B2 | 8/2008 | Peschmann |
| 7,418,077 B2 | 8/2008 | Gray |
| 7,453,987 B1 | 11/2008 | Richardson |
| 7,471,764 B2 | 12/2008 | Kaval |
| 7,483,510 B2 | 1/2009 | Carver |
| 7,486,768 B2 | 2/2009 | Allman |
| 7,492,228 B2 | 2/2009 | Strange |
| 7,492,860 B2 | 2/2009 | Garms |
| 7,505,557 B2 | 3/2009 | Modica |
| 7,505,562 B2 | 3/2009 | Dinca |
| 7,517,149 B2 | 4/2009 | Agrawal |
| 7,519,148 B2 | 4/2009 | Kotowski |
| 7,525,101 B2 | 4/2009 | Grodzins |
| 7,526,064 B2 | 4/2009 | Akery |
| 7,551,714 B2 | 6/2009 | Rothschild |
| 7,551,718 B2 | 6/2009 | Rothschild |
| 7,555,099 B2 | 6/2009 | Rothschild |
| 7,558,370 B2 | 7/2009 | Sommer |
| 7,561,664 B2 | 7/2009 | Teslyar |
| 7,577,234 B2 | 8/2009 | Knoespel |
| 7,579,845 B2 | 8/2009 | Peschmann |
| 7,606,348 B2 | 10/2009 | Foland |

(56) References Cited

U.S. PATENT DOCUMENTS

| | | |
|---|---|---|
| 7,609,807 B2 | 10/2009 | Leue |
| 7,660,388 B2 | 2/2010 | Gray |
| 7,720,194 B2 | 5/2010 | Connelly |
| 7,720,195 B2 | 5/2010 | Allman |
| 7,742,568 B2 | 6/2010 | Smith |
| 7,769,133 B2 | 8/2010 | Carver |
| 7,783,004 B2 | 8/2010 | Kotowski |
| 7,783,005 B2 | 8/2010 | Kaval |
| 7,796,733 B2 | 9/2010 | Hughes |
| 7,817,776 B2 | 10/2010 | Agrawal |
| 7,826,589 B2 | 11/2010 | Kotowski |
| 7,831,012 B2 | 11/2010 | Foland |
| 7,835,495 B2 | 11/2010 | Harding |
| 7,844,027 B2 | 11/2010 | Harding |
| 7,856,081 B2 | 12/2010 | Peschmann |
| 7,860,213 B2 | 12/2010 | Akery |
| 7,864,920 B2 | 1/2011 | Rothschild |
| 7,869,566 B2 | 1/2011 | Edic |
| 7,876,879 B2 | 1/2011 | Morton |
| 7,876,880 B2 | 1/2011 | Kotowski |
| 7,881,426 B2 | 2/2011 | Basu |
| 7,899,232 B2 | 3/2011 | Gudmundson |
| 7,903,783 B2 | 3/2011 | Modica |
| 7,915,596 B2 | 3/2011 | Clothier |
| 7,924,978 B2 | 4/2011 | Harding |
| 7,924,979 B2 | 4/2011 | Rothschild |
| 7,928,400 B1 | 4/2011 | Diawara |
| 7,957,505 B1 | 6/2011 | Katz |
| 7,963,695 B2 | 6/2011 | Kotowski |
| 7,982,191 B2 | 7/2011 | Friedman |
| 7,984,940 B2 | 7/2011 | Chen |
| 7,991,133 B2 | 8/2011 | Mills |
| 7,995,705 B2 | 8/2011 | Allman |
| 7,995,707 B2 | 8/2011 | Rothschild |
| 8,003,949 B2 | 8/2011 | Ryge |
| 8,047,053 B2 | 11/2011 | Call |
| 8,054,938 B2 | 11/2011 | Kaval |
| 8,059,781 B2 | 11/2011 | Agrawal |
| 8,073,099 B2 | 12/2011 | Niu |
| 8,090,150 B2 | 1/2012 | Garms |
| 8,135,110 B2 | 3/2012 | Morton |
| 8,135,112 B2 | 3/2012 | Hughes |
| 8,138,770 B2 | 3/2012 | Peschmann |
| 8,170,177 B2 | 5/2012 | Akery |
| 8,199,996 B2 | 6/2012 | Hughes |
| 8,243,876 B2 | 8/2012 | Morton |
| 8,275,091 B2 | 9/2012 | Morton |
| 8,356,937 B2 | 1/2013 | Kotowski |
| 8,385,501 B2 | 2/2013 | Allman |
| 8,389,942 B2 | 3/2013 | Morton |
| 8,428,217 B2 | 4/2013 | Peschmann |
| 8,433,036 B2 | 4/2013 | Morton |
| 8,442,186 B2 | 5/2013 | Rothschild |
| 8,457,275 B2 | 6/2013 | Akery |
| 8,483,356 B2 | 7/2013 | Bendahan |
| 8,491,189 B2 | 7/2013 | Kotowski |
| 8,498,376 B2 | 7/2013 | Modica |
| 8,503,605 B2 | 8/2013 | Morton |
| 8,503,606 B2 | 8/2013 | Rothschild |
| 8,579,506 B2 | 11/2013 | Morton |
| 8,582,718 B2 | 11/2013 | Harding |
| 8,644,453 B2 | 2/2014 | Morton |
| 8,654,922 B2 | 2/2014 | Bendahan |
| 8,668,386 B2 | 3/2014 | Morton |
| 8,674,706 B2 | 3/2014 | Peschmann |
| 8,687,765 B2 | 4/2014 | Kotowski |
| 8,731,137 B2 | 5/2014 | Arroyo |
| 8,735,833 B2 | 5/2014 | Morto |
| 8,750,452 B2 | 6/2014 | Kaval |
| 8,774,357 B2 | 7/2014 | Morton |
| 8,798,232 B2 | 8/2014 | Bendahan |
| 8,805,011 B2 | 8/2014 | Delianski |
| 8,831,176 B2 | 9/2014 | Morto |
| 8,837,670 B2 | 9/2014 | Akery |
| 8,840,303 B2 | 9/2014 | Morton |
| 8,842,808 B2 | 9/2014 | Rothschild |
| 8,861,684 B2 | 10/2014 | Al-Kofahi |
| 8,879,791 B2 | 11/2014 | Drouin |
| 8,908,831 B2 | 12/2014 | Bendahan |
| 8,929,509 B2 | 1/2015 | Morton |
| 8,958,526 B2 | 2/2015 | Morton |
| 8,971,485 B2 | 3/2015 | Morton |
| 8,993,970 B2 | 3/2015 | Morton |
| 9,014,425 B2 | 4/2015 | Perron |
| 9,020,095 B2 | 4/2015 | Morton |
| 9,020,096 B2 | 4/2015 | Allman |
| 9,025,731 B2 | 5/2015 | Kotowski |
| 9,042,511 B2 | 5/2015 | Peschmann |
| 9,052,403 B2 | 6/2015 | Morton |
| 9,057,679 B2 | 6/2015 | Morton |
| 9,086,497 B2 | 7/2015 | Bendahan |
| 9,099,279 B2 | 8/2015 | Rommel |
| 9,111,331 B2 | 8/2015 | Parikh |
| 9,121,958 B2 | 9/2015 | Morton |
| 9,158,027 B2 | 10/2015 | Morton |
| 9,218,933 B2 | 12/2015 | Langeveld |
| 9,223,049 B2 | 12/2015 | Kotowski |
| 9,223,050 B2 | 12/2015 | Kaval |
| 9,223,052 B2 | 12/2015 | Morton |
| 9,268,058 B2 | 2/2016 | Peschmann |
| 9,274,065 B2 | 3/2016 | Morton |
| 9,279,901 B2 | 3/2016 | Akery |
| 9,285,498 B2 | 3/2016 | Carver |
| 9,310,322 B2 | 4/2016 | Panesar |
| 9,310,323 B2 | 4/2016 | Bendahan |
| 9,316,760 B2 | 4/2016 | Bendahan |
| 9,329,285 B2 | 5/2016 | Gozani |
| 9,332,624 B2 | 5/2016 | Morton |
| 9,417,060 B1 | 8/2016 | Schubert |
| 9,466,456 B2 | 10/2016 | Rommel |
| 9,516,460 B2 | 12/2016 | Ambrefe, Jr. |
| 9,535,019 B1 | 1/2017 | Rothschild |
| 9,733,385 B2 | 8/2017 | Franco |
| 9,915,752 B2 | 3/2018 | Peschmann |
| 2001/0021241 A1 | 9/2001 | Swift |
| 2002/0008655 A1 | 1/2002 | Haj-Yousef |
| 2002/0018542 A1 | 2/2002 | Fenkart |
| 2002/0045152 A1 | 4/2002 | Viscardi |
| 2002/0094064 A1 | 7/2002 | Zhou |
| 2003/0009202 A1 | 1/2003 | Levine |
| 2003/0025302 A1 | 2/2003 | Urffer |
| 2003/0043964 A1 | 3/2003 | Sorenson |
| 2003/0068557 A1 | 4/2003 | Kumashiro |
| 2003/0168317 A1 | 9/2003 | Fromme |
| 2003/0171939 A1 | 9/2003 | Yagesh |
| 2003/0179126 A1 | 9/2003 | Jablonski |
| 2003/0213184 A1 | 11/2003 | Hunt |
| 2003/0214407 A1 | 11/2003 | Sweatte |
| 2003/0216644 A1 | 11/2003 | Hall |
| 2003/0225612 A1 | 12/2003 | Desimone |
| 2003/0229506 A1 | 12/2003 | Scott |
| 2004/0017887 A1 | 1/2004 | Le |
| 2004/0051265 A1 | 3/2004 | Nadeau |
| 2004/0077943 A1 | 4/2004 | Meaney |
| 2004/0120454 A1 | 6/2004 | Ellenbogen |
| 2004/0125914 A1 | 7/2004 | Kang |
| 2004/0141584 A1 | 7/2004 | Bernardi |
| 2004/0252024 A1 | 12/2004 | Huey |
| 2004/0258194 A1 | 12/2004 | Chen |
| 2004/0258198 A1 | 12/2004 | Carver |
| 2005/0023479 A1 | 2/2005 | Grodzins |
| 2005/0024199 A1 | 2/2005 | Huey |
| 2005/0057354 A1 | 3/2005 | Jenkins |
| 2005/0058242 A1 | 3/2005 | Peschmann |
| 2005/0074086 A1 | 4/2005 | Pendergraft |
| 2005/0100135 A1 | 5/2005 | Lowman |
| 2005/0111618 A1 | 5/2005 | Sommer, Jr. |
| 2005/0117683 A1 | 6/2005 | Mishin |
| 2005/0117700 A1 | 6/2005 | Peschmann |
| 2005/0135668 A1 | 6/2005 | Polichar |
| 2005/0137942 A1 | 6/2005 | Lafleur |
| 2005/0157842 A1 | 7/2005 | Agrawal |
| 2005/0169421 A1 | 8/2005 | Muenchau |
| 2005/0180542 A1 | 8/2005 | Leue |

(56) References Cited

U.S. PATENT DOCUMENTS

| | | |
|---|---|---|
| 2005/0193648 A1 | 9/2005 | Klein |
| 2005/0198226 A1 | 9/2005 | Delia |
| 2006/0023835 A1 | 2/2006 | Seppi |
| 2006/0027751 A1 | 2/2006 | Kurita |
| 2006/0056584 A1 | 3/2006 | Allman |
| 2006/0086794 A1 | 4/2006 | Knowles |
| 2006/0087439 A1 | 4/2006 | Tolliver |
| 2006/0114477 A1 | 6/2006 | Cox |
| 2006/0140341 A1 | 6/2006 | Carver |
| 2006/0145771 A1 | 7/2006 | Strange |
| 2006/0182221 A1 | 8/2006 | Bernhardt |
| 2006/0215811 A1 | 9/2006 | Modica |
| 2006/0249685 A1 | 11/2006 | Tanaka |
| 2006/0257005 A1 | 11/2006 | Bergeron |
| 2006/0284094 A1 | 12/2006 | Inbar |
| 2007/0085010 A1 | 4/2007 | Letant |
| 2007/0140423 A1 | 6/2007 | Foland |
| 2007/0172129 A1 | 7/2007 | Tortora |
| 2007/0189454 A1 | 8/2007 | Georgeson |
| 2007/0210255 A1 | 9/2007 | Bjorkholm |
| 2007/0228284 A1 | 10/2007 | Polichar |
| 2007/0237293 A1 | 10/2007 | Singh |
| 2007/0280502 A1 | 12/2007 | Paresi |
| 2008/0037707 A1 | 2/2008 | Rothschild |
| 2008/0048872 A1 | 2/2008 | Frank |
| 2008/0084963 A1 | 4/2008 | Clayton |
| 2008/0128624 A1 | 6/2008 | Cooke |
| 2008/0159591 A1 | 7/2008 | Ruedin |
| 2008/0170670 A1 | 7/2008 | Bhatt |
| 2008/0198967 A1 | 8/2008 | Connelly |
| 2008/0198970 A1 | 8/2008 | Kirshner |
| 2008/0205594 A1 | 8/2008 | Bjorkholm |
| 2008/0230709 A1 | 9/2008 | Tkaczyk |
| 2008/0260097 A1 | 10/2008 | Anwar |
| 2008/0267350 A1 | 10/2008 | Gray |
| 2008/0292050 A1* | 11/2008 | Goodenough ......... G01V 5/005 378/57 |
| 2008/0304622 A1 | 12/2008 | Morton |
| 2009/0067575 A1 | 3/2009 | Seppi |
| 2009/0074138 A1 | 3/2009 | Knoespel |
| 2009/0075325 A1 | 3/2009 | Das |
| 2009/0082047 A1 | 3/2009 | Phillips |
| 2009/0086907 A1 | 4/2009 | Smith |
| 2009/0116617 A1 | 5/2009 | Mastronardi |
| 2009/0127459 A1 | 5/2009 | Neustadter |
| 2009/0167042 A1 | 7/2009 | Chen |
| 2009/0168958 A1 | 7/2009 | Cozzini |
| 2009/0168964 A1 | 7/2009 | Safai |
| 2009/0238336 A1 | 9/2009 | Akery |
| 2009/0245462 A1 | 10/2009 | Agrawal |
| 2009/0252295 A1 | 10/2009 | Foland |
| 2009/0257555 A1 | 10/2009 | Chalmers |
| 2009/0284343 A1 | 11/2009 | Ambrefe, Jr. |
| 2009/0285353 A1 | 11/2009 | Ellenbogen |
| 2009/0316851 A1 | 12/2009 | Oosaka |
| 2010/0020937 A1 | 1/2010 | Hautmann |
| 2010/0034451 A1 | 2/2010 | Hughes |
| 2010/0119038 A1* | 5/2010 | Suyama ............ G01N 23/04 378/57 |
| 2010/0158191 A1 | 6/2010 | Gray |
| 2010/0161504 A1 | 6/2010 | Casey |
| 2010/0166141 A1* | 7/2010 | Vermilyea ............ H01J 35/10 378/19 |
| 2010/0177868 A1 | 7/2010 | Smith |
| 2010/0177873 A1 | 7/2010 | Chen |
| 2010/0295689 A1 | 11/2010 | Armistead |
| 2011/0019797 A1 | 1/2011 | Morton |
| 2011/0019799 A1 | 1/2011 | Shedlock |
| 2011/0038453 A1 | 2/2011 | Morton |
| 2011/0064192 A1 | 3/2011 | Morton |
| 2011/0075808 A1 | 3/2011 | Rothschild |
| 2011/0080999 A1 | 4/2011 | Kaval |
| 2011/0081099 A1 | 4/2011 | Hughes |
| 2011/0096901 A1 | 4/2011 | Kotowski |
| 2011/0129063 A1 | 6/2011 | Bendahan |
| 2011/0150174 A1* | 6/2011 | Sainath ............ A61B 6/4429 378/9 |
| 2011/0204243 A1 | 8/2011 | Bendahan |
| 2011/0216881 A1 | 9/2011 | Modica |
| 2011/0235777 A1 | 9/2011 | Gozani |
| 2011/0266643 A1 | 11/2011 | Engelmann |
| 2012/0099710 A1 | 4/2012 | Kotowski |
| 2012/0104276 A1 | 5/2012 | Miller |
| 2012/0116720 A1 | 5/2012 | Klann |
| 2012/0288060 A1 | 11/2012 | Beneke |
| 2013/0001048 A1 | 1/2013 | Panesar |
| 2013/0034268 A1 | 2/2013 | Perron |
| 2013/0126299 A1 | 5/2013 | Schoepe |
| 2013/0294574 A1 | 11/2013 | Peschmann |
| 2014/0003575 A1 | 1/2014 | Padgett |
| 2014/0104034 A1 | 4/2014 | Ambrefe, Jr. |
| 2014/0185771 A1 | 7/2014 | Morton |
| 2014/0192954 A1 | 7/2014 | Hanley |
| 2014/0197321 A1 | 7/2014 | Bendahan |
| 2015/0036798 A1 | 2/2015 | Morton |
| 2015/0078519 A1 | 3/2015 | Morton |
| 2015/0154876 A1 | 6/2015 | Modica |
| 2015/0245167 A1 | 8/2015 | Bobrow |
| 2015/0301220 A1 | 10/2015 | Morton |
| 2015/0330917 A1 | 11/2015 | Morton |
| 2015/0355117 A1 | 12/2015 | Morton |
| 2015/0355369 A1 | 12/2015 | Morton |
| 2016/0025888 A1 | 1/2016 | Peschmann |
| 2016/0025889 A1 | 1/2016 | Morton |
| 2016/0033674 A1 | 2/2016 | Allman |
| 2016/0084984 A1 | 3/2016 | Franco |
| 2017/0016997 A1* | 1/2017 | Shindou ............ G01T 1/2008 |
| 2018/0128936 A1 | 5/2018 | Franco |
| 2018/0299580 A1 | 10/2018 | Morton |

FOREIGN PATENT DOCUMENTS

| | | |
|---|---|---|
| CN | 1846151 | 10/2006 |
| CN | 101083757 | 12/2007 |
| CN | 102099708 A | 6/2011 |
| CN | 101185006 | 1/2013 |
| EP | 0077018 A1 | 4/1983 |
| EP | 0919186 A2 | 6/1999 |
| EP | 1413898 A1 | 4/2004 |
| EP | 1635169 A1 | 3/2006 |
| GB | 2255634 A | 11/1992 |
| GB | 2299251 | 9/1996 |
| GB | 2409268 A | 6/2005 |
| GB | 2424065 A | 9/2006 |
| GB | 2438317 A | 11/2007 |
| JP | S56103359 | 8/1981 |
| JP | 2002082070 A | 3/2002 |
| JP | 2002131244 | 5/2002 |
| WO | 9855851 A1 | 12/1998 |
| WO | 1999021148 | 4/1999 |
| WO | 2004010127 A1 | 1/2004 |
| WO | 2005098400 A2 | 10/2005 |
| WO | 2006027122 | 3/2006 |
| WO | 2006036076 A1 | 4/2006 |
| WO | 2006053279 A2 | 5/2006 |
| WO | 2006078691 A2 | 7/2006 |
| WO | 2007035359 A2 | 3/2007 |
| WO | 2007055720 A2 | 5/2007 |
| WO | 2007068933 A1 | 6/2007 |
| WO | 2007103216 A2 | 9/2007 |
| WO | 2008017983 A2 | 2/2008 |
| WO | 2009106803 A2 | 9/2009 |
| WO | 2009143169 A1 | 11/2009 |
| WO | 2011069024 A1 | 6/2011 |
| WO | 2011091070 A2 | 7/2011 |
| WO | 2013116549 | 8/2013 |
| WO | 2013119423 A1 | 8/2013 |
| WO | 2014107675 | 7/2014 |
| WO | 2014121097 A1 | 8/2014 |
| WO | 2014124152 A2 | 8/2014 |

(56) References Cited

FOREIGN PATENT DOCUMENTS

| WO | 2016011205 | 1/2016 |
| WO | 2016115370 A1 | 7/2016 |

OTHER PUBLICATIONS

International Search Report for PCT/US06/00623, dated Feb. 27, 2008, International Search Authority, pp. 12-13 of the report analyzes the materiality of certain references.
Second office action for Chinese Application No. CN201180021243.8, dated Jan. 6, 2015.
Third office action for Chinese Application No. CN201180021243.8, dated Aug. 31, 2015.
Notice of Allowance dated Feb. 3, 2015 for U.S. Appl. No. 14/249,657.
Examination Report for application No. GB20120015372, dated Oct. 23, 2014.
Supplementary European Search Report for EP11748209, completed on Sep. 13, 2017.
Office Action dated Nov. 13, 2018 for U.S. Appl. No. 15/408,737 (pp. 1-18).
International Search Report for PCT/US2017/013864, dated May 25, 2017.
First Office Action for Chinese Patent Application No. 201480052112X, dated Dec. 28, 2017.
Supplementary European Search Report for EP14829045, dated Feb. 17, 2017.
Office Action dated Jan. 7, 2016 for U.S. Appl. No. 14/338,435.
International Search Report for PCT/US2015/040653, dated Dec. 16, 2015.
International Search Report for PCT/US14/56652, dated Apr. 27, 2015.
International Search Report for PCT/US14/14198, dated May 16, 2014.
International Preliminary Report on Patentability for PCT/US2014/014198, dated Aug. 4, 2015.
International Search Report for PCT/US11/21758; dated Jul. 7, 2011, Rapiscan Systems Inc.
International Preliminary Report on Patentability for PCT/US11/21758, dated Jul. 7, 2011.
Written Opinion on Patentability for PCT/US11/21758; dated Jul. 7, 2011; Rapiscan Systems.
Molchanov P A et al: 'Nanosecond gated optical sensors for ocean optic applications' Sensors Applications Symposium, 2006. Proceedings of the 2006 IEEE Houston, Texas,USA Feb. 7-9, 2006, Piscataway, NJ, USA,IEEE, Feb. 7, 2006 (Feb. 7, 2006), pp. 147-150, XP010917671 ISBN: 978-0-7803-9580-0.
Mobile X-Ray Inspection Systems, Internet Citation, Feb. 12, 2007, pp. 1-2, URL:http://web.archive.org/web/20070212000928/http://www.bombdetecti- on.com/cat--details.php?catid=20.
International Search Report for PCT/GB09/00575, dated Apr. 7, 2010.
International Search Report for PCT/GB2009/000497, dated Jan. 22, 2010.
Smith C. R. et al: 'Application of 450 kV computed tomography to engine blocks with steel liners' Materials Evaluation vol. 65, No. 5, 2007, pp. 458-461, XP055108238.
International Search Report for PCT/US13/23676, dated Jun. 28, 2013.
International Search Report for PCT/US13/24191, Rapiscan Systems Inc., dated Jun. 25, 2013.
International Search Report for PCT/US2014/010370, dated May 13, 2014.
International Search Report for PCT/US10/58809; Rapiscan Systems Inc.; dated Apr. 19, 2011.
International Search Report for PCT/US2014/015126, dated May 27, 2014.
Written Opinion of the International Searching Authority for PCT/US2014/015126, dated May 27, 2014.
Office Action dated Oct. 14, 2016 for U.S. Appl. No. 14/338,435.
Office Action dated Apr. 27, 2017 for U.S. Appl. No. 14/338,435.
Notice of Allowance dated Sep. 27, 2017 for U.S. Appl. No. 14/338,435; (pp. 1-13).
Office Action for Australian Patent Application No. 2014293215, dated May 1, 2018.
Office Action for Japanese Patent Application No. 2016-529850, dated Apr. 12, 2018.
International Search Report for PCT/US2012/054110, dated Dec. 24, 2012.
Office Action dated Oct. 12, 2017 for U.S. Appl. No. 14/996,018; (pp. 1-7).
Sheen, David et al. 'Three-Dimensional Millimeter-Wave Imaging for Concealed Weapon Detection', Sep. 2001, IEEE Transactions on Microwave Theory and Techniques, vol. 49, No. 9, pp. 1581-1592.
'Test and Evaluation Plan for Screener Proficiency Evaluation and Reporting System (SPEARS) Threat Image Projection' J.L.Fobes, Ph.D., et al. FAA, Dec. 1995.
'Revised Test and Evaluation Plan for Determining Screener Training Effectiveness' Brenda A. Klock, et al. FAA, Aug. 2000.
'Development and Validation of a Test of X-ray Screener Readiness' Eric C. Neiderman, Ph.D., et al. IEEE, 2000.
Rapiscan Security Products, Inc., Users Guide for Level 3 Threat Image Projection (TIP) System Manual, Aug. 4, 1999, document in general.
International Search Report for PCT/GB2006/000690, dated Aug. 21, 2006.
Rapiscan X-ray Machines HM Prison Contract T601/00, 'Rapiscan', Rapiscan Security Products Ltd., p. 1-2, 1999-2000.
Office Action dated Dec. 31, 2014 for U.S. Appl. No. 13/489,377.
Notice of Allowance dated Jan. 13, 2015 for U.S. Appl. No. 13/858,479.
Office Action dated Mar. 18, 2015 for U.S. Appl. No. 14/165,177.
Notice of Allowance dated Aug. 20, 2015 for U.S. Appl. No. 14/165,177.
Notice of Allowance dated Dec. 7, 2015 for U.S. Appl. No. 13/489,377.
Examination Report for European Patent Application No. 06709915, dated Feb. 16, 2015.
Rapiscan Security Products, Inc., Users Guide for Levels 1 and 2 Threat Image Protection (TIP) Users Manual, Jan. 12, 2001, document in general.
Rapiscan 520S High Performance Compact X-ray Machine, 'Rapiscan', Rapiscan Security Products Ltd., p. 1, 2003.
Office Action dated Dec. 30, 2016 for U.S. Appl. No. 14/684,089.
Office Action dated Jun. 23, 2017 for U.S. Appl. No. 14/684,089; (pp. 1-9).
Examination Report for European Patent Application No. 06709915, dated Nov. 18, 2016.
Notice of Allowance dated Oct. 26, 2017 for U.S. Appl. No. 14/684,089; (pp. 1-8).
Communication under Rule 71(3) for European Patent Application No. 06709915, dated Dec. 12, 2017.
Office Action dated Sep. 27, 2011 for U.S. Appl. No. 13/023,516.
International Search Report for PCT/US2016/013441, dated May 5, 2016.
Office Action dated Apr. 9, 2018 for U.S. Appl. No. 14/996,018 (pp. 1-9).
Extended European Search Report for EP16737893.4, dated Jul. 25, 2018.

* cited by examiner

PORTABLE X-RAY SCANNER

CROSS-REFERENCE

The present specification relies on U.S. Patent Provisional Application No. 62/219,589, of the same title and filed on Sep. 16, 2015, for priority.

FIELD

The present specification discloses security systems for X-ray inspection, in particular portable X-ray security inspection systems having a compact profile.

BACKGROUND

X-ray security inspection machines are widely used at security checkpoints, such as those in airports, malls, courthouses, government offices, embassies, schools, and prisons. Where space is not restricted or where an X-ray security inspection machine is required on a permanent basis, the machine may be set up and configured on site, and retained there indefinitely. Such machines are provided in various sizes and specifications, depending on their intended application.

Nevertheless, as the issue of security becomes an ever greater priority, there is an increasing demand for X-ray security inspection machines which find more widespread application. In particular, there is a need for X-ray security inspection machines which may be employed in space-restricted environments and/or which are readily moveable, i.e. portable, from one location to another. Most of the currently available machines are heavy, bulky, and not readily portable. Additionally, most of the currently available security screening systems cannot be easily and efficiently deployed in outdoor environments or at temporary venues, where they are frequently needed to scan for threats inside small baggage items such as backpacks and purses. Typically, tedious and sometimes ineffective hand-searches of small items must be performed.

In most X-ray systems, a highly collimated continuous wave (CW) X-ray source is used, which covers the objects being scanned with a thin fan beam. This has an advantage that a relatively inexpensive linear array of dual-energy detectors can be used for generating the image, while providing the capability of organic/inorganic discrimination based on a thin front detector to detect lower-energy X-rays and a thicker rear detector to detect higher-energy X-rays. The ratio of low-to-high-energy X-ray signal is used for material discrimination. However, a limitation of this approach is that most of the X-rays emitted by the source are absorbed in the collimator, and the X-ray source has to be on continuously to cover the full extent of the object. This leads to a required large amount of shielding in all directions except for the forward fan beam, and also power consumption is high. Such systems therefore tend to be heavy and/or bulky, making them difficult to transport from one place to another.

Dual-energy imaging is typically used to image bags and parcels in the security industry. In X-ray baggage scanners, however, a line array of dual-layer detectors is used. The detector layer closest to an X-ray source is used to primarily detect low-energy X-rays and the detector layer furthest from the source, usually filtered by some filtration material such as copper, is used to primarily detect high-energy X-rays. A width of the detector is typically on the order of 1 mm, and a continuous X-ray source is required to scan objects 1 mm or so, at a time. With an intense X-ray source that is collimated to a fan beam, objects can be scanned at speeds of the order of 20 cm/s. All other X-rays emitted by the source need to be stopped by shielding.

There is a need, therefore, for an improved X-ray security inspection system that may be employed in space-restricted environments and/or which is readily moveable, i.e. portable, from one location to another. Also, there is a need for a security inspection system that is compact, light-weight, and can be ported to temporary and/or outdoor venues.

SUMMARY

In some embodiments, the present specification discloses a portable X-ray imaging system, comprising: a housing defining a tunnel for receiving an article to be inspected; a conveyor for conveying the article through the tunnel at a pre-defined speed; an X-ray production system positioned within said housing, comprising: a first X-ray source pulsed at a first time to generate a first electron beam along a first longitudinal axis, wherein said first X-ray source is positioned above the conveyor; a second X-ray source pulsed at a second time to generate a second electron beam along a second longitudinal axis, wherein the first and second X-ray sources are positioned opposing to each other, wherein the second time is different than the first time, and wherein said second X-ray source is positioned above the conveyor; a target positioned between the first and second X-ray sources, wherein the target has a first side facing the first X-ray source and a second side facing the second X-ray source, wherein the first electron beam strikes the first side at a first impact point to generate a first X-ray cone beam and the second electron beam strikes the second side at a second impact point to generate a second X-ray cone beam, and wherein respective apexes of the first and second X-ray cone beams are separated by a distance; and an X-ray detector system positioned within said housing and comprising at least one two-dimensional flat panel detector for generating a first image of the article corresponding to the first X-ray cone beam and a second image of the article corresponding to the second X-ray cone beam, wherein the first and second sides of the target are inclined at an angle with respect to a top surface plane of said at least one detector.

Optionally, the first X-ray source is operated at a first voltage and the second X-ray source is operated at a second voltage, and wherein the second voltage is higher than the first voltage.

Optionally, an angle of inclination of the first side relative to the top surface plane of the at least one detector ranges from 10 to 45 degrees and wherein an angle of inclination of the second side relative to the top surface plane of the at least one detector ranges from 10 to 45 degrees.

Optionally, the first and second longitudinal axes are non-collinear and lie on a single plane. Optionally, the first longitudinal axis lies at a first angle relative to the first side and the second longitudinal axis lies at a second angle relative to the second side, wherein said first and second angles are less than or equal to 10 degrees.

Optionally, the distance ranges from 1 cm to 5 cm.

Optionally, a difference between the first and second times is defined such that the first image overlaps the second image as the article is conveyed at the pre-defined speed.

Optionally, the two-dimensional flat panel detector has a first layer, a second layer of a first thickness positioned on top of said first layer, a third layer of a second thickness positioned on top of said second layer, and a fourth layer of a third thickness positioned on top of said third layer.

Optionally, a first additional layer is included between said first and second layers and a second additional layer is included between said third and fourth layers.

In some embodiments, the present specification is directed toward a portable X-ray imaging system, comprising: a housing defining a tunnel for receiving an article to be inspected; a conveyor for conveying the article through the tunnel at a pre-defined speed; an X-ray production system positioned within said housing, comprising: a first X-ray source pulsed at a first time to generate a first electron beam along a first longitudinal axis; a second X-ray source pulsed at a second time to generate a second electron beam along a second longitudinal axis, wherein the first and second X-ray sources are positioned opposing to each other, and wherein the second time is greater than the first time; a target positioned between the first and second X-ray sources, wherein the target has a first side facing the first X-ray source and a second side facing the second X-ray source, wherein the first electron beam strikes the first side at a first impact point to generate a first X-ray cone beam and the second electron beam strikes the second side at a second impact point to generate a second X-ray cone beam, and wherein respective apexes of the first and second X-ray cone beams are separated by a distance; and an X-ray detector system positioned within said housing and comprising at least one two-dimensional flat panel detector for generating a first image of the article corresponding to the first X-ray cone beam and a second image of the article corresponding to the second X-ray cone beam, wherein the first and second sides of the target are inclined at an angle with reference to a top surface plane of said at least one detector, and wherein said at least one detector has a first layer, a second layer of a first thickness positioned on top of said first layer, a third layer of a second thickness positioned on top of said second layer, and a fourth layer of a third thickness positioned on top of said third layer.

Optionally, said first layer comprises an amorphous silicon or CMOS detector substrate, said second layer comprises a color filter, said third layer comprises a first scintillator material that emits scintillation light in a first color, and said fourth layer comprises a second scintillator material that emits scintillation light in a second color.

Optionally, said first thickness is less than 1 mm but greater than 0 mm, said second thickness ranges from less than 1 mm to 3 mm, and said third thickness is less than 1 mm but greater than 0 mm.

Optionally, said first layer predominantly detects high energy X-rays while said fourth layer predominantly detects low energy X-rays.

Optionally, a first additional layer is included between said first and second layers and a second additional layer is included between said third and fourth layers.

Optionally, at least one of said first additional layer and second additional layer are fiber-optic plates.

Optionally, said second layer is deposited on said first additional layer, wherein said first additional layer comprises a fiber-optic plate.

Optionally, a first additional layer is positioned below said second layer such that said second layer is adjacent to said first additional layer and wherein the first additional layer comprises a fiber-optic plate.

Optionally, at least one of said first additional layer and second additional layer comprises a third scintillator material that emits scintillation light in a third color.

Optionally, said second layer is configured to permit two or more colors to penetrate there through.

Optionally, the first electron beam defines a first plane and the second electron beam defines a second plane and wherein the first plane and second plane are positioned proximate to each other within a range of 0 mm to 3 mm.

In some embodiments, the present specification is directed toward an X-ray transmission imaging system and method, comprising: a housing defining an X-ray tunnel for receiving an article to be inspected; a conveyor for conveying the article through the tunnel; an X-ray source for irradiating the article within the tunnel, comprising at least one source for generating X-ray beams; and an X-ray detector system, wherein the X-ray detector system comprises at least one two-dimensional flat panel detector for detecting X-ray beams.

In some embodiments, the present specification is directed toward an X-ray transmission imaging system, comprising: a housing defining an X-ray tunnel for receiving an article to be inspected; a conveyor for conveying the article through the tunnel; an X-ray source for irradiating the article within the tunnel, comprising at least one source for generating X-ray beams; and an X-ray detector system, wherein the X-ray detector system comprises at least one two-dimensional flat panel detector for detecting X-ray beams; and wherein either the source is capable of producing different X-ray energies, or the detector is capable of measuring two or more X-ray spectra simultaneously, or both.

Optionally, the X-ray source comprises at least one X-ray source that may be pulsed. Still optionally, the X-ray source pulses with alternating high and low energies.

Optionally, the X-ray source is a continuous source operated at low current. Optionally, said source is operated using a continuously changing high voltage that cyclically alternates, for example using a sinusoidal or approximately square wave, between a low voltage and a high voltage.

Optionally, the X-ray production subsystem comprises two X-ray sources operating at different voltages.

Optionally, the flat panel detector is covered with a scintillator material.

Optionally, the two-dimensional flat panel detector uses a first layer of flat panel detectors and a second layer of flat panel detectors, and wherein the first layer of flat panel detectors acts as a filter for the second layer of flat panel detectors. Still optionally, the first layer of flat panel detectors is covered with a scintillator material of a first thickness and the second layer of flat panel detectors is covered with a scintillator material of a second thickness, and wherein the first thickness is less than the second thickness. Optionally, there is additional filtration material, such as copper sheet, between the first layer and the second layer.

Optionally, the system includes a touchscreen interface to operate the system. Still optionally, the touchscreen interface comprises a bright screen.

Optionally, the system includes handles on either end of the system.

Optionally, the system comprises a gurney, wherein the system is placed over the gurney. Still optionally, the gurney is foldable.

In some embodiments, the detector system comprises a substrate layer; a color filter placed over the substrate layer; an intermediate layer of a first scintillator material placed over the color filter, the intermediate layer emitting scintillation light in a first color; and a top layer of a second scintillator layer placed over the intermediate layer, the top layer emitting scintillation light in a second color. The color filter may be patterned in multiple sections (e.g., checkerboard) that alternately permit two or more colors to penetrate, where the color filter sections are matched to one or the other of the color spectra emitted by the two scintillators.

In some embodiments, the detector system comprises: a substrate layer; a first fiber-optic plate placed over the substrate layer; a color filter placed over the first fiber optic plate; an intermediate layer of a first scintillator material placed over the color filter, the intermediate layer emitting scintillation light in a first color; a second fiber-optic plate places over the intermediate layer; and a top layer of a second scintillator layer placed over the intermediate layer, the top layer emitting scintillation light in a second color. Optionally, the fiber-optic plate can be replaced with a non-fiber-optic but transparent plate, e.g., made of glass. Optionally, the second plat may incorporate, a second (but not patterned) color filter.

The aforementioned and other embodiments of the present shall be described in greater depth in the drawings and detailed description provided below.

BRIEF DESCRIPTION OF THE DRAWINGS

These and other features and advantages of the present invention will be appreciated, as they become better understood by reference to the following detailed description when considered in connection with the accompanying drawings, wherein.

DETAILED DESCRIPTION

The present specification discloses multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present specification is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

It should be noted herein that any feature or component described in association with a specific embodiment may be used and implemented with any other embodiment unless clearly indicated otherwise.

One of ordinary skill in the art would appreciate that the features described in the present application can operate on any computing platform including, but not limited to: a laptop or tablet computer; personal computer; personal data assistant; cell phone; server; embedded processor; DSP chip or specialized imaging device capable of executing programmatic instructions or code.

It should further be appreciated that the platform provides the functions described in the present application by executing a plurality of programmatic instructions, which are stored in one or more non-volatile memories, using one or more processors and presents and/or receives data through transceivers in data communication with one or more wired or wireless networks.

Figure 1:
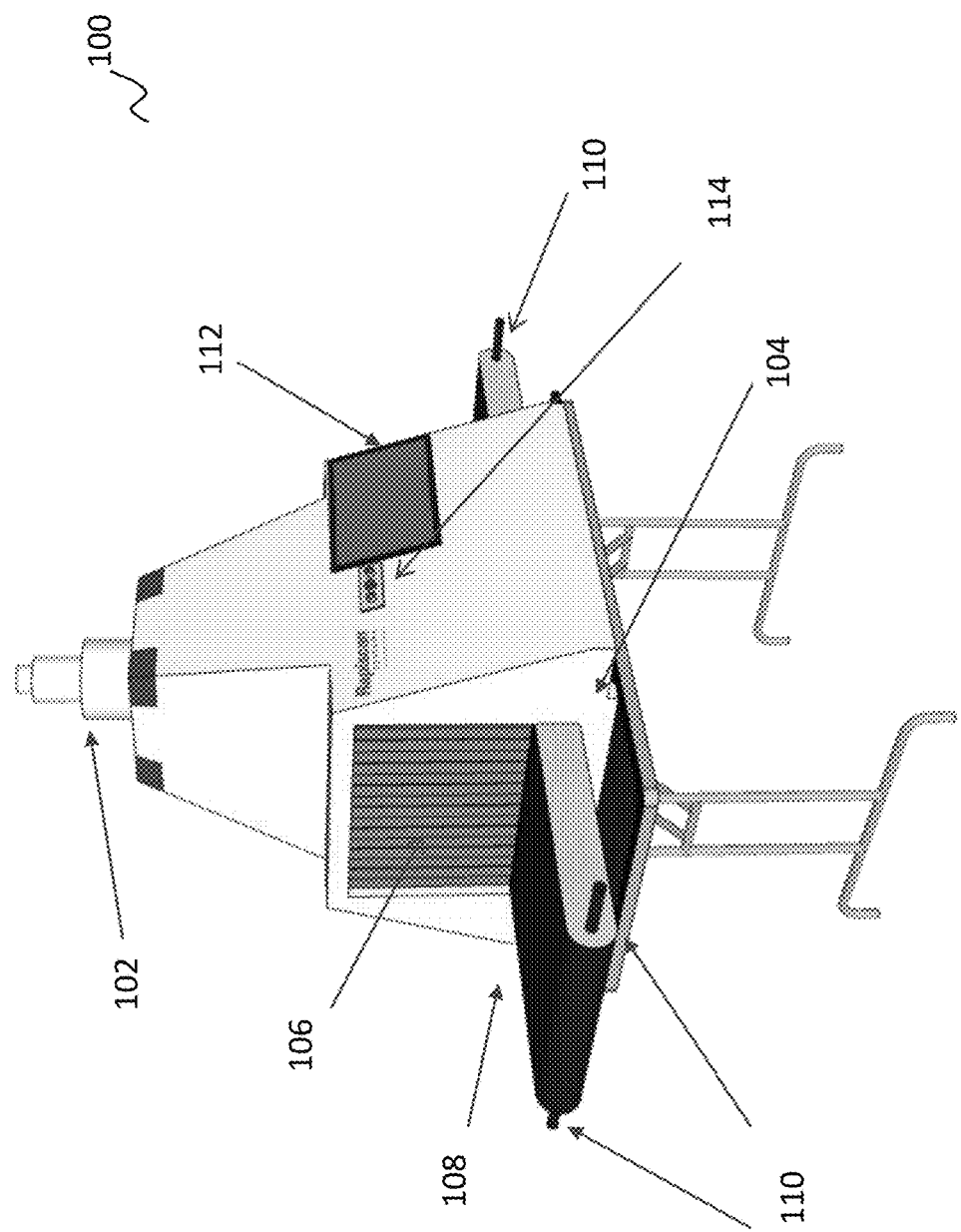
FIG. 1 illustrates an overview of a compact X-ray inspection system, in accordance to an embodiment described in the present specification.

FIG. 1 illustrates an overview of a compact X-ray inspection system 100, in accordance with an embodiment described in the present specification. System 100 may be a portable and light-weight X-ray scanning system. System 100 may be configured to scan small baggage items such as backpacks, purses, or any other small items, in order to identify firearms, 0.5 lbs. or more of explosives, or any other concealed material that may be contraband or poses a security risk. Embodiments of system 100 include at least an X-ray source 102, a two-dimensional (2D) detector array 104, a machine housing defining an X-ray tunnel 106 for receiving an article to be inspected, and optionally, a conveyor 108 for conveying the article through the tunnel 106. In other optional embodiments, any system or mechanism for moving the object or source and detector may be used to obtain a full image of the object. X-ray source 102 may irradiate X-ray beams that are detected by detector array 104. Additionally, handles 110 may be provided at corners of system 100 to enable handling of system 100 while transporting it as a single unit from one place to another. System 100 may communicate with an interface 112 that allows monitoring of articles under inspection through images scanned by system 100 through detector array 104. Interface 112 may also enable a user to control operation of system 100. In embodiments, interface 112 may be a touchscreen interface. In embodiments, the screen of interface 112 may be back-lit brightly during its operation such that display of interface 112 is visible when system 100 is placed in an outdoor environment. In embodiments, interface 112 is the primary interface to system 100, in addition to some cabinet X-ray requirements such as emergency-off buttons and perhaps forward and backward scan buttons 114. An optional shade may be designed in case the screen of interface 112 is not bright enough for operation in direct sunlight. In embodiments, operator assist algorithms may be programmed within system 100, which help users/operators analyze cluttered images. In embodiments, automated threat detection algorithms are implemented within system 100.

Figure 6:
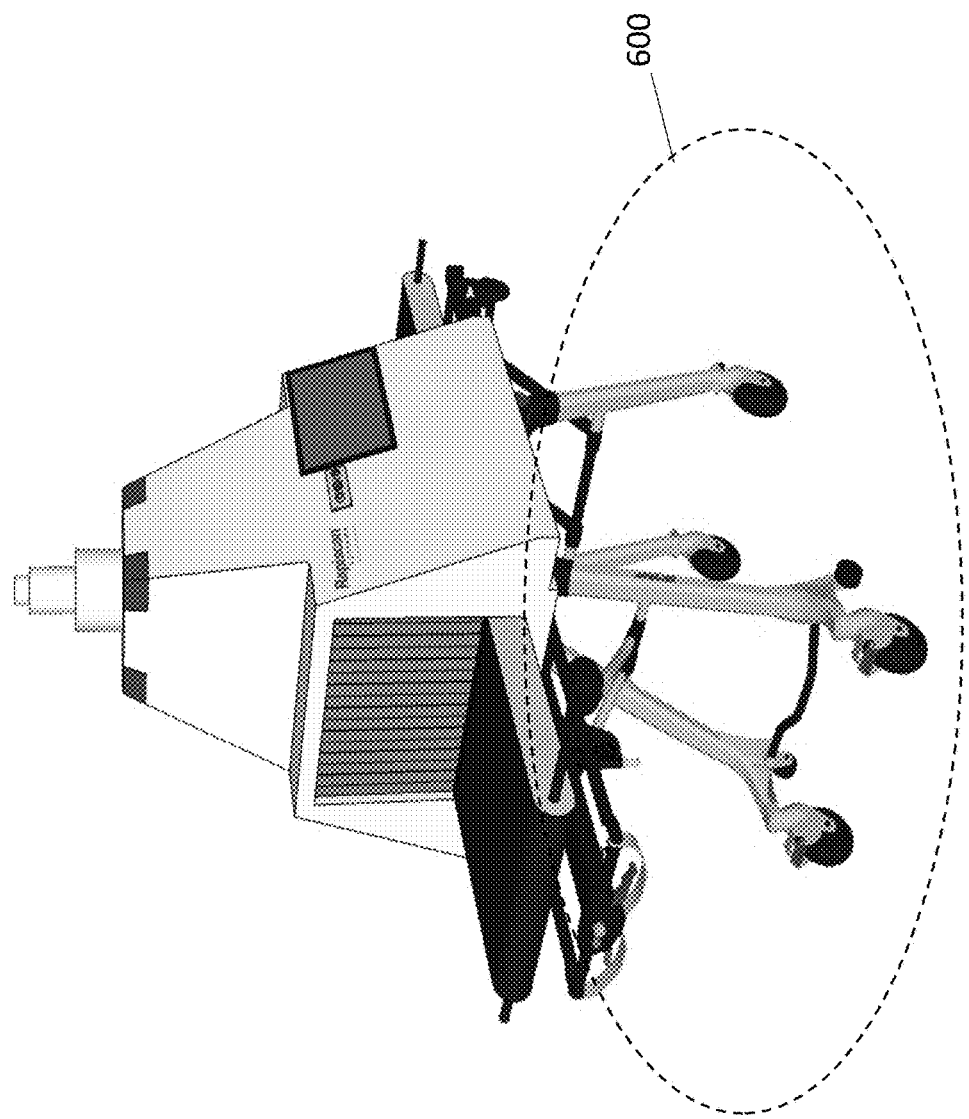
FIG. 6 illustrates an exemplary foldable wheeled-carriage used with an embodiment of the system of the present specification.

Referring to FIG. 6, a foldable wheeled carriage 600 may be used, much like the gurney used in ambulances, to allow transportation of system 100. Use of carriage 600 may allow easy stowing of system 100 in a van with rails for this purpose.

X-Ray Source

A large-area dual-energy detector system may be useful when used with a cone-beam pulsed X-ray source, relative to a collimated beam X-ray source. The cone beam may cover a large section of an object under inspection with each X-ray pulse, therefore saving power and allowing high throughput. Moreover, more of the X-rays produced by such a source may be used for scanning, resulting in lower shielding requirements in all other directions, which directly translates into lower system weight.

Figure 2:
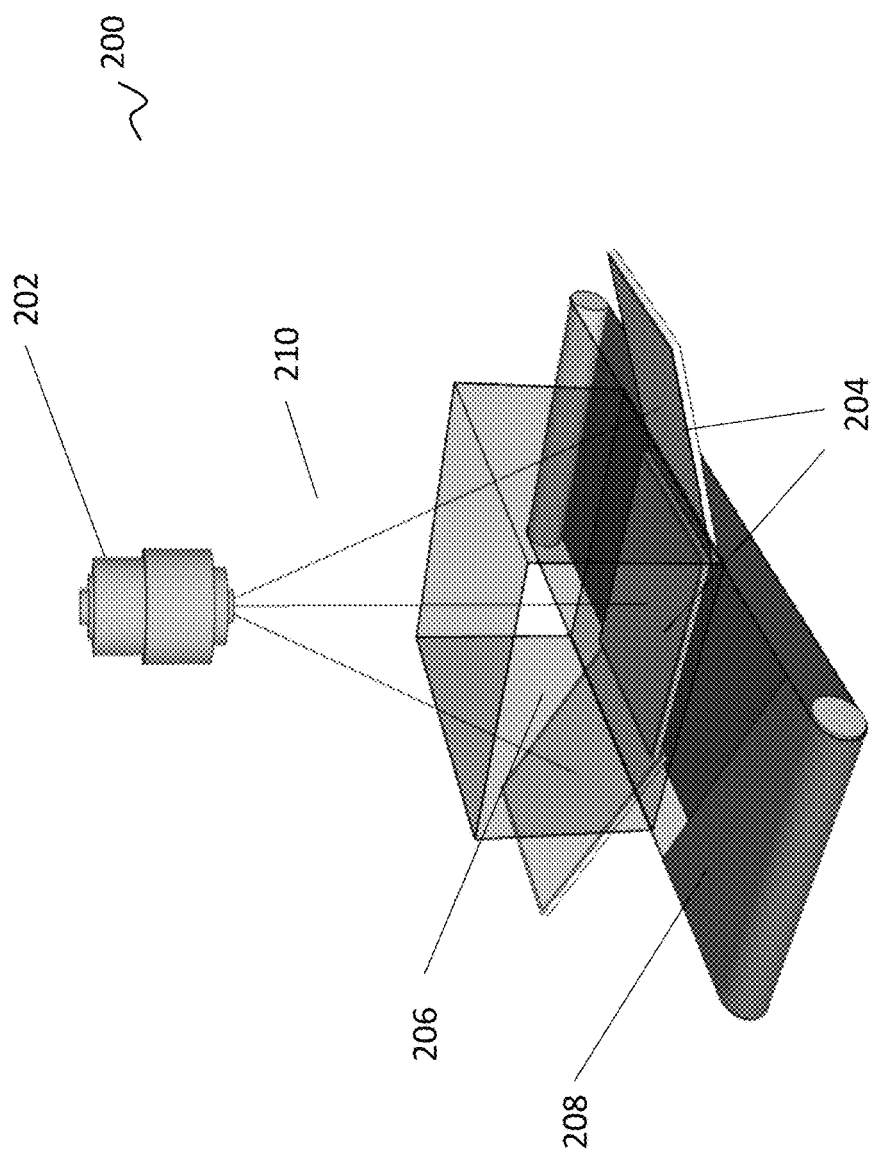
FIG. 2 illustrates an exemplary X-ray inspection system with an X-ray source irradiating a set of 2D detectors with a wide-angle X-ray beam.

FIG. 2 illustrates an exemplary X-ray inspection system 200 with an X-ray source 202 producing a wide-angle beam 210 and irradiating one or more detectors 204. In embodiments, X-ray source 202 is a pulsed X-ray source of between 100 kV and 300 kV with a wide-angle beam. With each X-ray pulse, beam 210 thus covers a large section of an object under inspection that may pass through a tunnel 206 over a conveyor belt 208. As a result, X-ray source 202 may utilize less power and allow high throughput, relative to conventional compact X-ray inspection systems. Additionally, the configuration of source 202 may enable more of the X-ray beams produced by source 202 to be used for scanning, resulting in lower shielding requirements in all other directions, translating into lower weight of system 200.

Typical flat-panel detectors 204 can be up to 17 by 17 inches in size, in which case two or three of them could be sufficient to image objects. For a use case where only very small objects are imaged, a single detector could be sufficient, with an appropriately sized smaller tunnel. In a preferred embodiment, a larger number of smaller panels may be employed, such as 4×6 inch panels, in which case 10 or 12 small panels may be employed. The panels would be arranged to as close as possible intercept the X-rays from the source at 90 degrees at their center, or whichever arrangement is compatible with regards to locations and dimensions of other components, such as the belt.

Most security systems require an ability of material discrimination in order to distinguish organic and inorganic items, or distinguish one item from another, inside an object under inspection. In embodiments, dual-energy images are created to meet this requirement. In one embodiment, source 202 comprises a dual-energy X-ray source. The voltage setting of source 202 may be varied to achieve dual-energy imaging. In examples, source 202 voltage settings for this type of imaging are 50-90 kVp and 100-160 kVp. In embodiments, switching sources may be employed to switch between different voltage settings of source 202. In an embodiment two closely spaced X-ray sources with different voltages may be used for dual-energy analysis. Optionally, the X-ray source is a continuous source operated at low current. Optionally, said source is operated using a continuously changing high voltage that cyclically alternates, for example using a sinusoidal or approximately square wave, between a low voltage such as 50-90 kVp and a high voltage such as 100-160 kVp.

The system of the present specification may be embodied in different shapes and sizes such that the objectives of the present invention are achieved. In an embodiment, the X-ray housing has a pyramid structure. As shown in FIG. 2, the shape can be of any shape as long as the X-rays from the source can be collimated to irradiate the full area (or most of the full area) of the detector array below. While collimation would happen close to the source using a collimator, there would still be scattered X-rays from walls of the housing, from the conveyor belt, from the detectors and from the object being inspected. Thus, the housing has to be constructed so as to (1) let the cones of X-rays that illuminate the detectors pass through without encountering too much material (with the exception of the tunnel through which the bag travels, which should be made, in the area where the X-ray beam passes through, of a reasonably X-ray transparent material, such as aluminum or carbon fiber); (2) prevent X-rays, in any other direction, from exiting the housing and causing a radiation dose to operators and others; and (3) be optimized for light weight. The housing can further be designed such that it keeps operators and/or personnel and any exposed body parts as far away as possible from any remaining sources of primary or scattered radiation, such that applicable cabinet X-ray standards are satisfied.

Referring back to FIG. 1, in an exemplary embodiment, tunnel 106 is 60 centimeters (cm) wide and 40 cm high. In an exemplary embodiment system 100 has approximate dimensions of 40 inches height, 60 inches length, and 36 inches width. In an exemplary embodiment, system 100 weighs approximately 100 lbs.

Figure 3A:
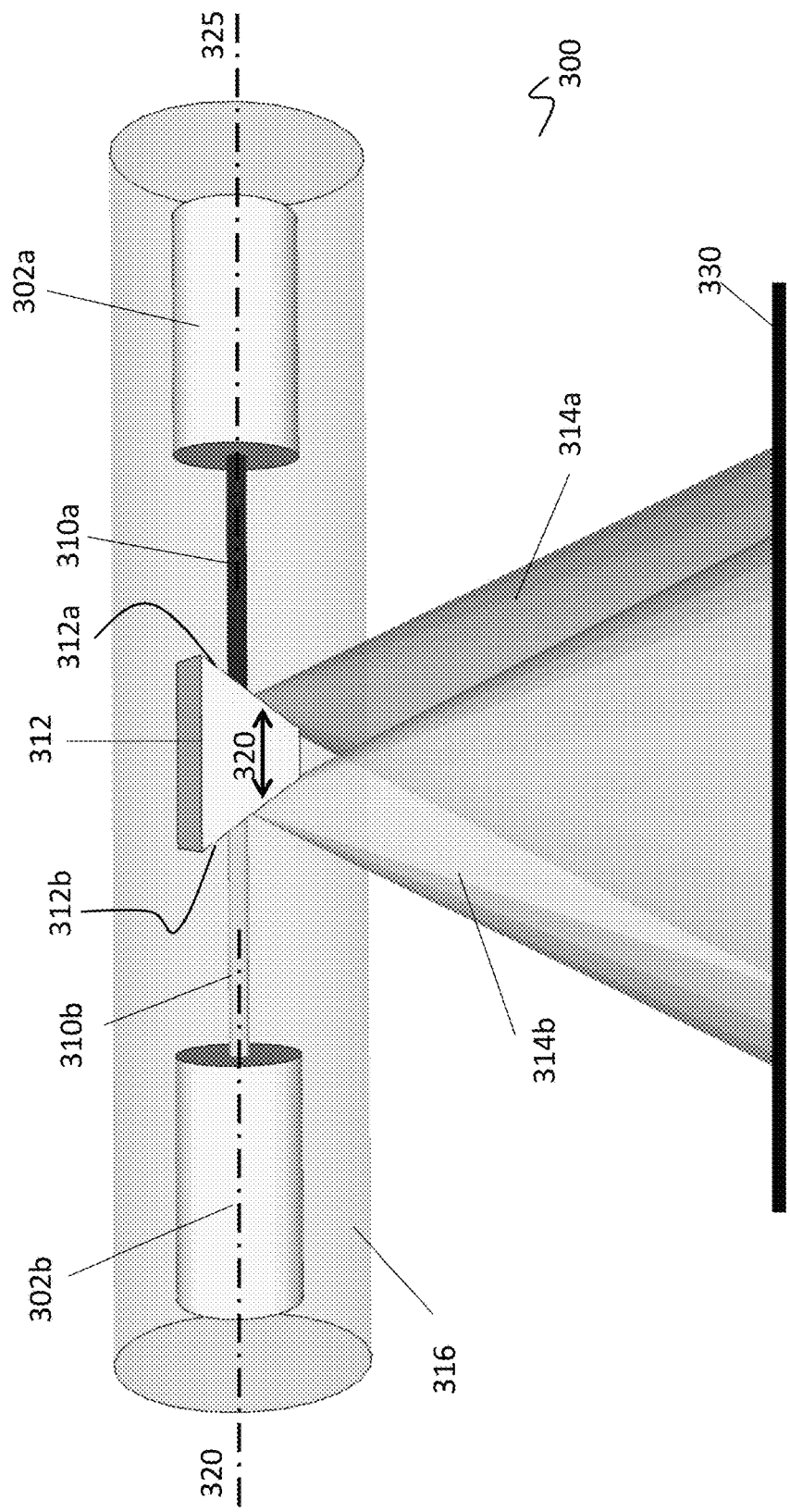
FIG. 3A illustrates a dual-energy pulsed source-ray production system, in accordance with an embodiment of the present specification.
Figure 3B:
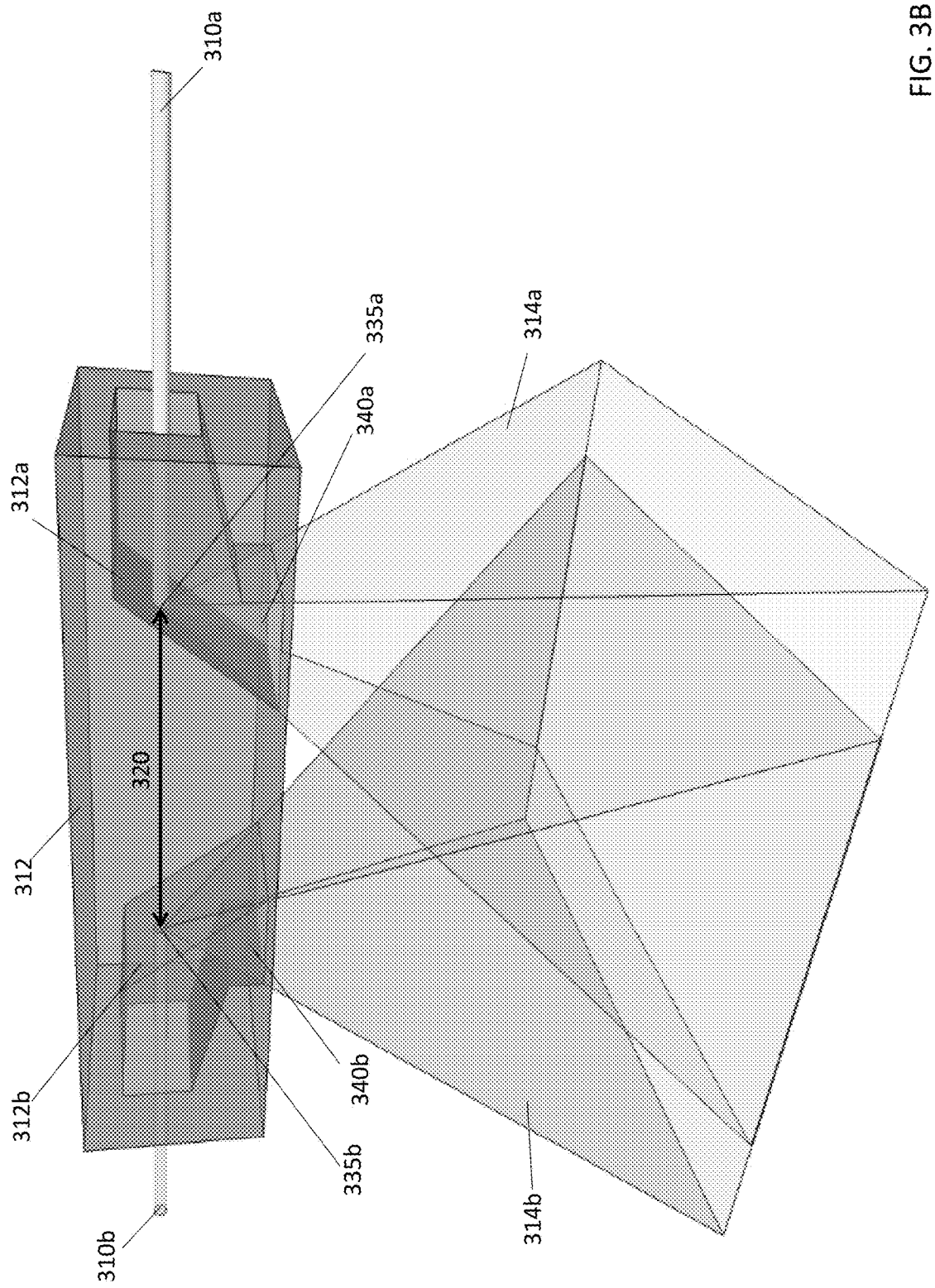
FIG. 3B shows a target with built-in shielding and collimation, in accordance with an embodiment of the present specification.

FIG. 3A illustrates a dual-energy pulsed X-ray production system 300 while FIG. 3B shows a target 312 with built-in shielding and collimation, in accordance with an embodiment of the present specification. Referring now to FIGS. 3A and 3B simultaneously, the system 300 comprises a first single-energy pulsed X-ray source 302a and a second single-energy pulsed X-ray source 302b positioned in opposition to each other. A target 312 is positioned between the first and second X-ray sources 302a, 302b. In some embodiments, the target 312 is positioned symmetrically to lie in the middle of the X-ray sources 302a, 302b. However, in alternate embodiments the target 312 is asymmetrically positioned between the two sources 302a, 302b such that the target 312 is closer to one source and commensurately farther from the other source. The target 312 comprises a first side or surface 312a facing the first X-ray source 302a and a second side or surface 312b facing the second X-ray source 302b.

In embodiments, at a time t1, the first X-ray source 302a produces a first pulsed beam 310a of electrons along a first longitudinal axis 320. The first electron beam 310a is accelerated over a high voltage V1 to strike the first side 312a of the target 312 at a first impact point 335a, producing X-rays more or less in the shape of a cone of X-rays 314a having its apex at the first impact point 335a. Similarly, at a time t2, which is later than t1, the second source 302b produces a second pulsed beam 310b of electrons along a second longitudinal axis 325. The second electron beam 310b is accelerated over a high voltage V2, where V2 is different from V1, to strike the second side 312b of the target 312 at a second impact point 335b, the second side 312b being opposite to the first side 312a, producing X-rays more or less in the shape of a cone of X-rays 314b having its apex at the second impact point 335b.

In some embodiments, the first and second longitudinal axes 320, 325 are substantially parallel and aligned to each other such that the axes 320, 325 lie in the same plane. In some embodiments, the first and second longitudinal axes 320, 325 are substantially parallel to each other but lie on different planes such that the respective planes of the two axes 320, 325 are separated by a distance of less than 3 mm and preferably not more than 1 mm. In still other embodiments, the first and second longitudinal axes 320, 325 are angled with respect to each other and may or may not lie on the same plane. In one embodiment, the axes 320, 325 are mutually inclined at angles of up to 10 degrees but lie on the same plane. In another embodiment, the axes 320, 325 are mutually inclined at angles of up to 10 degrees and lie in different respective planes that are separated by a distance of less than 3 mm and preferably not more than 1 mm.

Accordingly, it is advantageous for the two impact points 335a, 335b of the electron beams (the apexes of the X-ray cones 314a and 314b) to be an equal distance away from a plane of the detectors 330 such that they are in the same plane, within a tolerance of a few mm, for example within a tolerance of less than 3 mm, so that the images generated by the two X-ray beams 314a, 314b are "commensurate", that is, appear to have the same magnification. Further, as shown in FIG. 3B, the X-rays 314a, 314b are generated respectively inside two wide cones 340a, 340b with their respective tips at the electron beam impact points 335a, 335b. Shielding occurs in part by the target 312 itself, so the cones 314a, 314b are limited in at least one direction by the first and second sides 312a, 312 of the target 12 that, in various embodiments, are inclined at an angle with reference to the plane of the detector 330. X-ray emitted in all directions other than the two wide cones 340a, 340b are shielded. Since the emission of X-rays from the target 312 depends only weakly on the incoming electron beam direction, the electron beams do not have to be perfectly aligned. Thus, in some embodiments, the non-collinearity of the electron beam axes 320 and 325 can be up to 10 degrees. It is advantageous, however, for each impact point (also known as a "beam spot") 335a, 335b to not move by more than a millimeter or so in any direction during operation, since moving spots affect imaging resolution, and adversely affect image registration between the two images generated by the two X-ray cone beams 314a, 314b. Slow spot movement over time (also referred to as "drift") is not as serious in this case since a large cone beam is used on a large-area detector as it is with a finely collimated fan beam in typical prior art applications since in prior art applications this drift leads to intensity fluctuations. In various embodiments, the size of the beam spots 335a, 335b is about 1 mm since larger spot sizes lead to lower imaging resolution.

In various embodiments, the respective planes of the first and second sides or surfaces 312a, 312b are angled or inclined with reference to the plane of the detectors 330 (positioned at the bottom relative to the target 312 and X-ray sources 302a, 302b). In various embodiments, the respective planes of the first and second sides 312 are inclined at angles ranging from 5 to 75 degrees and preferably from 10 to 45 degrees with respect to the plane of the detectors 330. In embodiments, the plane of the detectors 330 is substantially horizontal. In some embodiments, the target 312 is configured in the form of an inverted trapezoid having the first and second opposing sides 312a, 312b as shown in FIG. 3A. However, the target 312 can be of any polygonal shape as long as it includes the first and second opposing sides or surfaces 312a, 312b inclined at an angle with reference to the plane of the detectors 330 thereby allowing the X-rays 314a, 314b to be emitted in the direction of the detectors 330. As shown in FIG. 3B, the target 312 includes built-in shielding to block X-rays in all directions, other than the direction of the detectors 330, thereby requiring reduced external shielding.

In embodiments, the parts of the first and second sides 312a, 312b that are being struck by the electron beams are thin layers of tungsten which are typically of the order of having a thickness of less than 1 mm, although other materials may be employed. The remainder of the target material could be any material, for example copper or aluminum, such that the target 312 can conduct both heat and electricity. In a case where the voltages of the first and second sides 312a, 312b are not the same (in the case where the cathodes are at ground potential but the target 312 is not), an insulating material that is capable of withstanding the voltage difference between the two halves of the target 312 is used to separate the two halves of the target 312. For example, in that use scenario, each half of the target 312 may be comprised of a first layer, which may be a thin layer of tungsten on top of a second layer, which may be a layer of copper or aluminum for heat and electricity conduction.

The overall dimensions of the target 312 depend on the desired angle of inclination of the first and second sides 312a, 312b. In various embodiments, the angular inclination of the first and second sides 312a, 312b is configured: a) so that the cones of X-rays 314a, 314b are emitted downwards onto the plane of the detectors 330 at the bottom side of the system 300, b) to generate a desired width of the cone beams 314a, 314b, and c) to have a desired distance 320 between the apexes of the two cones 314a, 314b of X-rays. In the case where the target 312 is split in two halves, the overall dimensions of the target 312 are dependent on the distance required to ensure that the voltage difference between the two halves can be sustained. In a typical configuration, but not limited to such configuration, it would be advantageous for the distance 320 between cone apexes to be small, for example 0.5 to 5 cm, and for the overall size of the target 312 to be slightly larger than that, for example 1 to 7 cm in the direction of measurement of the distance 'd' (as shown by the double-pointed arrow 320.

In embodiments, system 300 is surrounded by an enclosure 316. Enclosure 316 may be constructed to be opaque to X-rays except for a window at the bottom of enclosure 316 to allow passage for conical beams 314a and 314b.

The voltages V1 and V2, over which electron beams 310a and 310b are accelerated, may be produced in two ways. In one embodiment, a cathode of source 302a is kept at negative voltage V1, a cathode of source 302b is kept at negative voltage V2, and target 312 is an anode kept at electrical ground potential, thus producing a positive voltage difference for each source 302a and 302b.

In another embodiment, target 312 is split into two parts in the middle in a manner that an insulating material is inserted between the two parts. The part of target 312 facing source 302a may be an anode that is kept at positive high voltage V1, while the part of target 312 facing source 302b may also be an anode that is kept at positive high voltage V2. Cathodes of both sources 302a and 302b may be kept at ground potential.

In embodiments, an object being inspected is placed below system 300, in order to be imaged by a detector (not shown) placed below the object.

In embodiments, an image I1 is taken with a large-area 2D detector (known as a flat-panel detector), such as detector array 204 of FIG. 2. The image I1 may be taken at the time t1 using the X-rays from beam 314a. Another image I2 may be taken with the same detector at the time t2 using the X-rays from beam 314b. If the object being imaged is stationary, then the two images I1 and I2 will see the object from two different vantage points, determined by a distance (d) 320 between apexes of the two conical beams 314a and 314b.

In an embodiment, between time t1 and time t2, the object to be imaged using X-ray system 300 is moved by approximately distance d 320 between the apex of conical beams 314a and 314b, in a direction defined by locations of the first source 302a and the second source 302b. This could be arranged by means of conveyor belt 208 of FIG. 2 that runs at a velocity v equal to the distance d divided by the difference between the two times (t2−t1). Therefore, $$v=d/(t2-t1).$$

Alternatively, the difference in time between successive pulses could be adjusted in such a way as to ensure that the image taken with beam 314a at time t1 perfectly overlaps the image taken with beam 314b at time t2. In that case, $$t2-t1=d/v.$$

Since the two images I1 and I2 are now aligned properly, and since they were taken with X-ray beams 314a and 314b of different source voltages V1 and V2, a single dual-energy image may be constructed from the two images I1 and I2.

System 300 may repeat this process until the entire object is imaged. Following the X-ray pulses from source 302a and source 302b at times t1 and t2, another X-ray pulse using source 302a may be generated at a time t3 and another X-ray pulse using source 302b at a time t4. The time between pulses t3 and t4, i.e., t4−t3, may be selected to match the movement of the object, as explained before.

Figure 8:
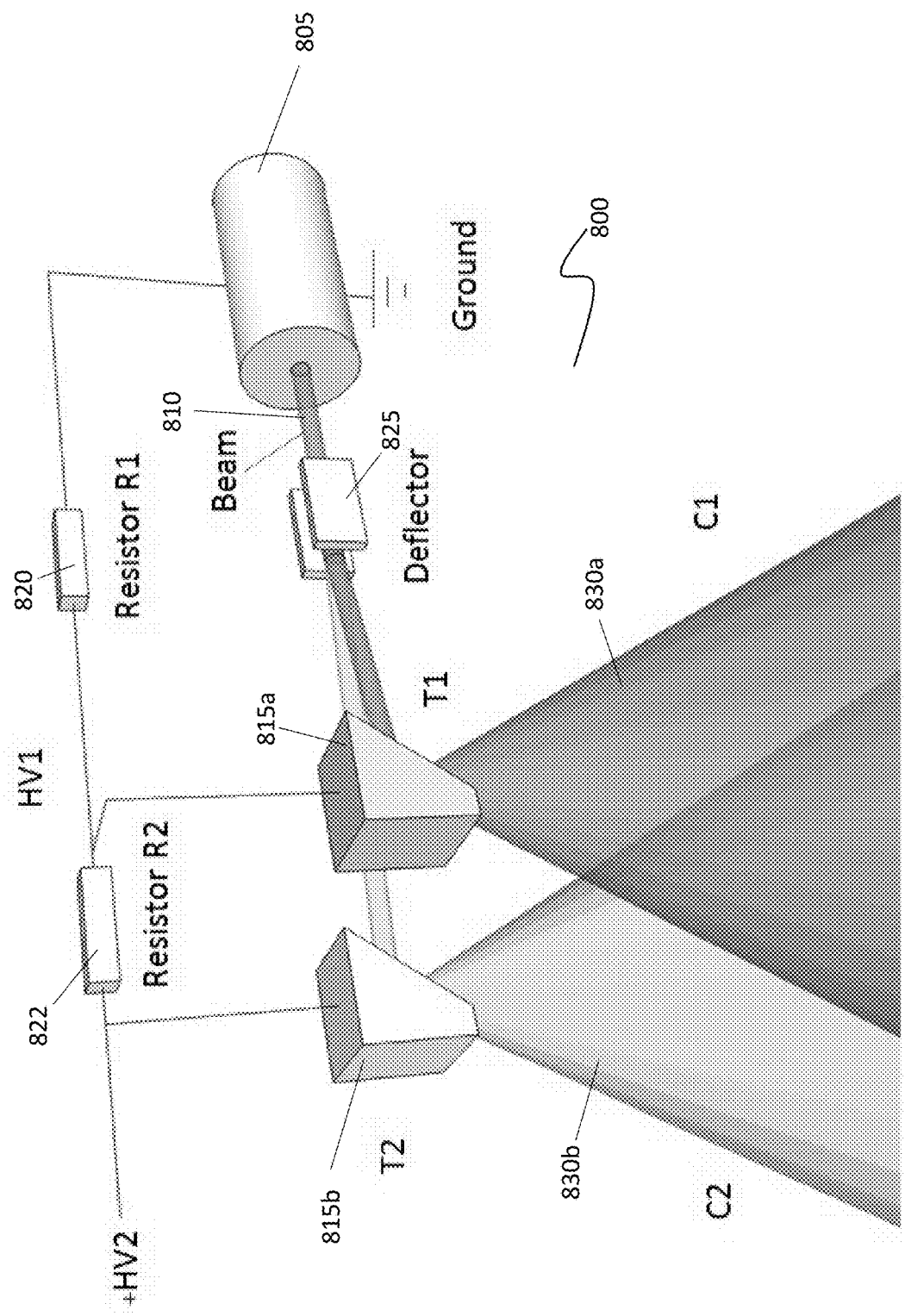

FIG. 8 illustrates a single beam dual-energy X-ray production system 800, in accordance with an embodiment of the present specification. The system 800 comprises a grounded electron beam generator or source 805 emitting an electron beam 810 that is configured to alternately strike a first target 815a and a second target 815b. A positive high voltage HV2 is applied to the second target 815b. Through a conductive connection and resistors 820, 822 the voltage drops to ground voltage for the source 805. The conductive connection between resistors 820, 822 is also connected to the first target 815a which is maintained at a voltage HV1. Values of the resistors 820, 822 are chosen such that the voltage HV1 on the first target 815a is lower than the voltage HV2 on the second target 815b but higher than ground potential.

During operation, the electron beam 810 passes through a deflector 825. When, at a first time t1, a first low voltage v1 is applied to the deflector 825, the beam 810 deflects in the direction of the first target 815a to strike the first target 815a and produce a first X-ray cone 830a with maximum X-ray energy determined by voltage HV1. When, at a second time t2 which is greater than t1, a second low voltage v2 is applied to the deflector 825 (wherein the second voltage v2 is lower than the first voltage v1 and possibly of a sign opposite to that of voltage v1), the electron beam 810 deflects in the direction of the second target 815b to strike the second target 815b and produce a second X-ray cone 830b with maximum X-ray energy determined by voltage HV2. Accordingly, a switching dual-energy source is realized using the single electron beam generator 805. It should be appreciated that that it is much easier and faster to switch between low voltages v1 and v2 on the deflector 825 than between high voltages such as HV1 and HV2 using a switching source.

In various embodiments, the targets 815a, 815b are spaced sufficiently far apart to avoid high-voltage sparking to occur between the targets 815a, 815b due to the voltage difference (HV2−HV1) between the targets 815a, 815b. In embodiments, the distance between the two targets 815a, 815b is of the order of a few cm. In various embodiments, the targets 815a, 815b are appropriately shaped to avoid sharp protrusions which concentrate the field strength and can cause breakdown, as is known to persons of ordinary skill in the art.

In an alternate embodiment, the beam 810 is aimed exclusively at the second target 815b and no deflector is employed. The first target 815a, located closer to the electron beam generator 805, is inserted periodically into the beam 810 or on-demand by mechanical means. In one embodiment, this is accomplished by the first target 815a comprising a wheel with a conical edge, with at least one gap, rotating at a constant rate of rotation. The rotating wheel leads to situations where the electron beam 810 either strikes the conical edge of the first target 815a thereby producing X-ray cone 830a, or passes through a gap to strike the second target 815a to produce X-ray cone 830b. This embodiment has an advantage of not requiring a deflector and associated electronics, but has a disadvantage of requiring a moving target and mechanical and electrical means for moving the target.

Detector

Referring back to FIG. 2, in embodiments, 2D detector array 204 uses flat-panel detectors covered with scintillator material. Flat-panel detectors may be prepared using amorphous silicon or CMOS technologies. Embodiments of the present specification describe systems to allow dual-energy operation of detector 204 for organic/inorganic discrimination.

A large-area dual-energy detector system is useful when used with a cone-beam pulsed X-ray source or a cone-beam low-current continuous source, such as those described in various embodiments above. In order to detect X-rays, flat-panel detectors usually also have a layer of scintillator material. In some cases, there is also a fiber-optic plate, usually made of glass, between the scintillator and the detection layer, which collimates the scintillation light towards the pixels below. Examples of common scintillators include Cesium Iodide (CsI) and Gadolinium Oxi-Sulfide (GdOS). The panels are then read out pixel by pixel and the data are transferred to a computer for processing, interpretation and display.

Dual-energy images may be generated using such detectors. In one known method, dual-energy X-ray source system 300 of FIG. 3 is used. An image is acquired using one energy setting on detector 204, and sometime later a second image is acquired using a different energy setting. Typical source voltage settings for this type of imaging may be 50-90 kVp and 100-160 kVp. This technique is commonly known as "double shot".

In an alternative known method, two flat-panel detectors are arranged on top of one another, with an additional filtration material (such as a copper sheet) between the two detectors. Low-energy X-rays are primarily detected in an upper detector, while higher-energy X-rays are capable of penetrating both the upper detector and the filtration material, to be registered in a lower detector. This technique is known as "single shot".

Figure 4:
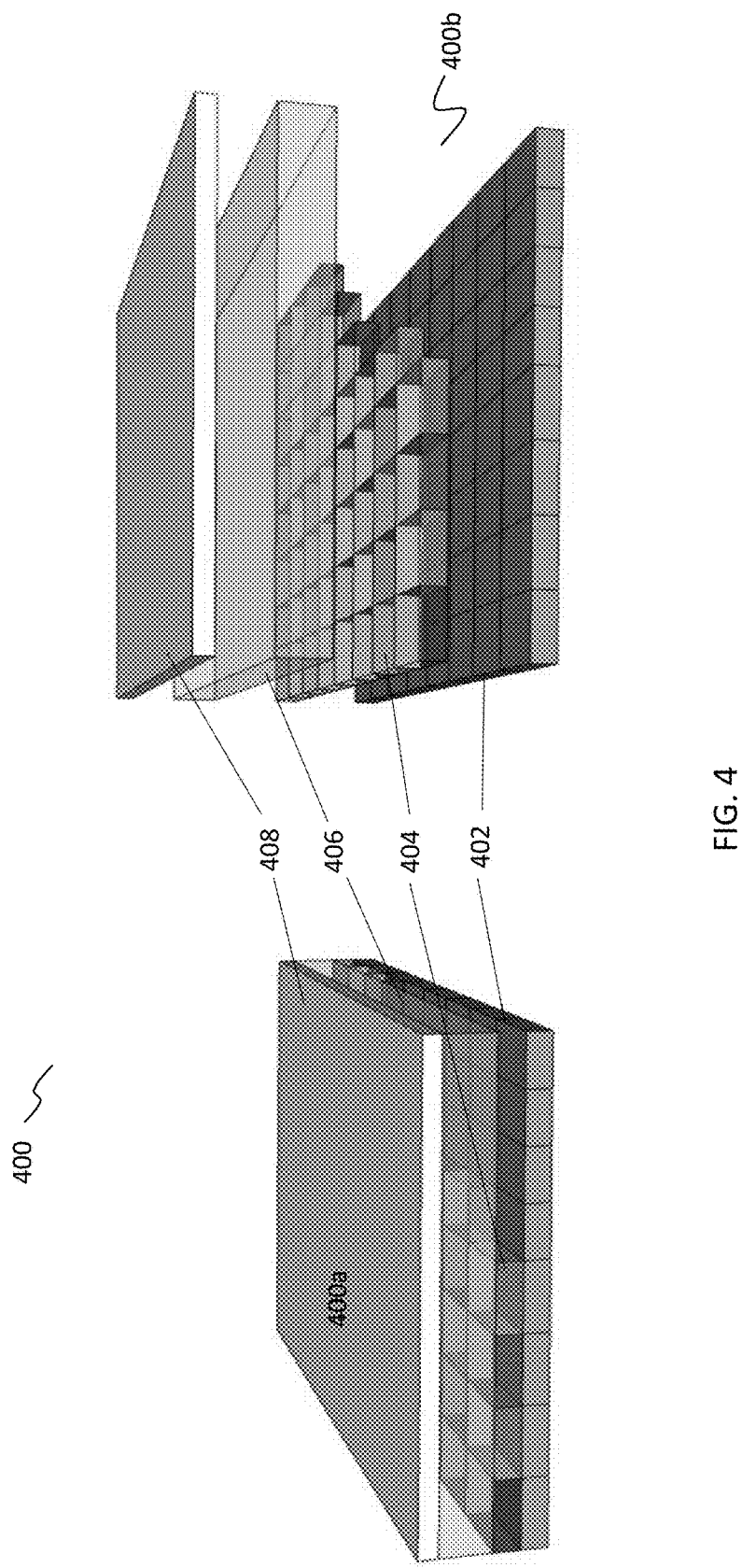
FIG. 4 illustrates a dual-energy large area flat-panel detector system, in accordance with an embodiment of the present specification.

FIG. 4 illustrates a dual-energy large area flat-panel detector system 400, in accordance with an embodiment of the present specification. Detector system 400 is shown in the figure through two different views—view 400a illustrates an assembled detector system 400, and view 400b depicts a disintegrated assembly of layers/components of detector system 400. In embodiments, detector system 400 may consist of four layers. A bottom layer 402 may be an amorphous silicon or CMOS detector substrate layer, a second layer 404 is a color filter, a third layer 406 may be an intermediate layer of scintillator material that emits scintillation light in one color. In an example, also used here for illustration purposes, scintillation light at layer 406 is of blue color, such as that derived from some plastic scintillators, or CsI(Na) for example. A final top layer 408 may consist of a mostly opaque screen-type scintillator that emits scintillation light in another color. In an example, also used here for illustration purposes, scintillation light at layer 408 is of red color, such as that derived from GdOS(Eu) screen material, for example. Since such screen material is usually white in appearance (i.e., it reflects all colors of optical light equally), it may also serve as a reflector for the light produced by intermediate layer 406 of scintillator material.

In various embodiments, a thickness of the top scintillator layer 408 is less than 1 mm but greater than 0 mm, a thickness of the intermediate scintillator layer 406 is of the order of less than 1 mm to 3 mm while the color filter second layer 404 is typically less than 1 mm thick but greater than 0 mm.

During operation, low-energy X-rays may be detected in the thin top scintillator layer 408, and scintillation light may be produced with the color spectrum of the type of scintillator used in that layer. For example, if top layer 408 is made of thin (0.1 to 0.5 mm, for example) red-emitting screen material, the light produced will be transmitted through intermediate layer 406 of scintillator material, and mostly detected by pixels covered by red parts of color filter 404. In embodiments, higher energy X-rays are mostly detected in the thicker intermediate layer 406 of scintillator material between top layer 408 and color filter 404. For example, if layer 406 is made, of 1 to 2 mm, of blue-emitting scintillator, this light would be detected mostly by the pixels below the blue parts of color filter 404.

Figure 5:
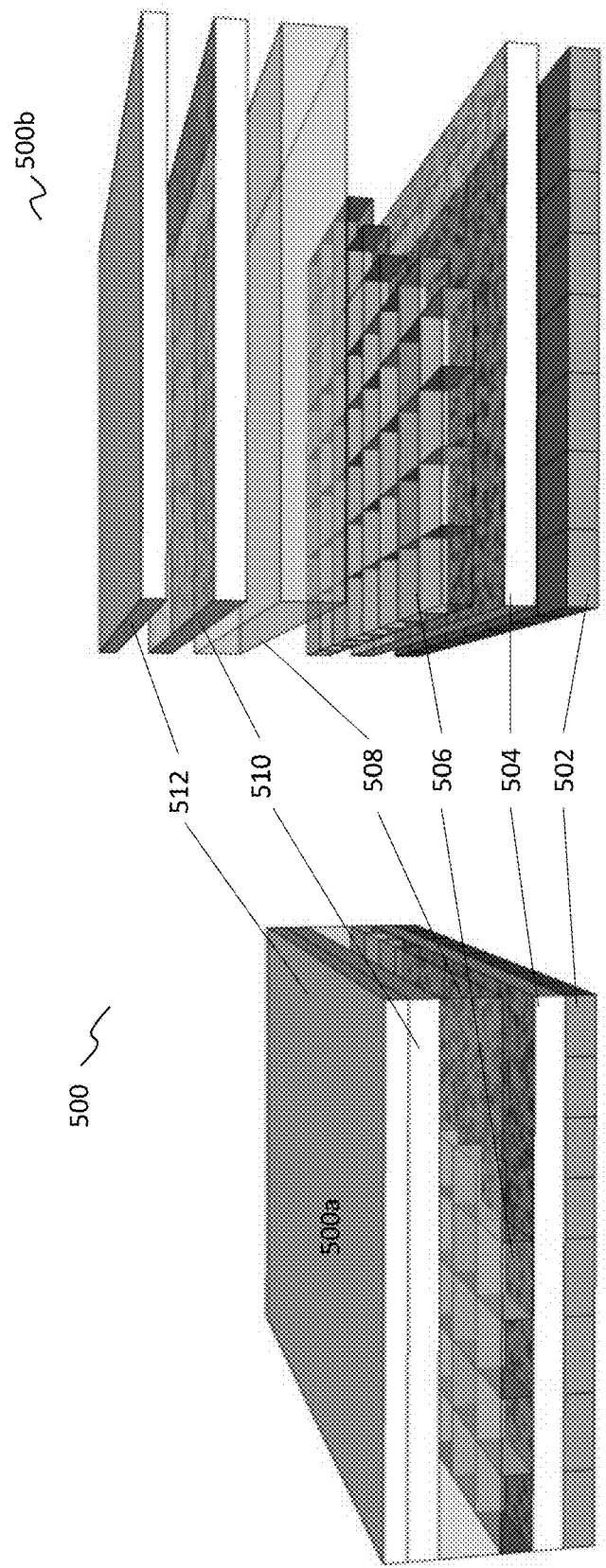
FIG. 5 illustrates an alternative embodiment of a detector system.

FIG. 5 illustrates an alternative embodiment of a dual energy detector system 500. Detector system 500 is shown in the figure through two different views—view 500*a* illustrates an assembled detector system 500, and view 500*b* depicts a disintegrated assembly of layers/components of detector system 500. In this embodiment, a fiber-optic plate 504 is included between a detector substrate layer 502 and a color filter 506. Additionally, a fiber-optic plate 510 is included between an intermediate scintillator layer 508 and a top scintillator layer 512. Fiber optic plate 504 is usually the layer that sits directly on top of detector substrate 502 in existing detector panels and may guide scintillation light down to the detector pixels, while eliminating light going in other directions, thereby advantageously increasing spatial resolution. It may be possible to deposit color filter 506 on fiber-optic plate 504 rather than on detector substrate 502 directly, with the advantage that no special modifications need to be made to detector substrate 502, and existing flat-panel detectors may be modified to produce a dual-energy flat-panel detector 500. In embodiments, color filter layer 506 is inverted along with fiber-optic plate 504 such that color filter 506 is adjacent to detector substrate 502. In embodiments, fiber-optic plate 504 is optional, and may be omitted. In embodiments, color filter layer 506 is deposited directly on detector substrate 502. In embodiments, color filter layer 506 is a separate layer that can be inserted where most advantageous.

The second fiber-optic plate 510 may be included between the two scintillator layers 508 and 512 in order to increase filtration of the X-rays between the two scintillator layers 508 and 512. A thickness of this fiber-optic plate 510 may be adjusted to provide the desired amount of X-ray filtration. In embodiments, one or both fiber-optic plates 504 and 510 may be replaced with simple glass plates or plates of another transparent material, or with leaded-glass plates that provide higher attenuation for the same thickness, or with a plate made of a third scintillation material emitting another color of scintillation light. In an embodiment where one or both fiber-optic plates 504 and 510 are replaced with a third scintillation material, suitable modifications are made to color filter 506 in order to take advantage of the third scintillator. In an embodiment, the second plate 510 also is or incorporates a second un-patterned color filter that eliminates or reduces any undesired part of the spectral range of light emitted by the top layer 512 of scintillator.

In various embodiments, a thickness of the top scintillator layer 512 is less than 1 mm but greater than 0 mm, a thickness of the intermediate scintillator layer 508 and of the fiber-optic plates 504, 510 is on the order of less than 1 mm to 3 mm while the color filter layer 506 is typically less than 1 mm thick but greater than 0 mm.

Color Filters

Color filters (404, 506 of FIGS. 4, 5 respectively) can be manufactured that efficiently divide the optical spectrum between two colors at a selectable wavelength. In various embodiments, the color filters (404, 506 of FIGS. 4, 5 respectively) are patterned in multiple sections (for example, checkerboard) that alternately permit two or more colors to penetrate. Embodiments of color filters, such as filters 404 and 506, are known for their use in CCDs for color cameras (Bayer filters, which are usually small but have very fine resolution) and in LCD panels (which can be very large). In embodiments, inkjet printers may be used to print color filters (404, 506) directly on substrates (402, 502).

Scintillators

In embodiments, standard scintillators are used with flat-panel detectors (400, 500 of FIGS. 4, 5 respectively). These may include scintillators using Terbium-doped Gadolinium Oxysulfide, with chemical formula $Gd_2O_2S(Tb)$, also called GdOS or Gadox, and Thallium-doped Cesium Iodide, with chemical formula CsI(Tl). Gadox screens may emit in the green part of a spectrum, with a maximum emission at around 550 nm. $Gd_2O_2S(Eu)$ may be used, which is a variety of Gadox that is doped with Europium, and it has its emission maximum in the red part of a spectrum around 630 nm.

In other embodiments, a scintillator material used is CsI that can be either doped with Sodium (Na), in which case it emits in the blue range of the spectrum (maximum emission near 400 nm), or with Thallium (Tl) in which case it emits in the green range of the spectrum (maximum emission near 550 nm). CsI can be made in thin sheets, with columnar microstructure that guides the scintillation light towards the detector pixels.

In yet other embodiments, plastic scintillator may be used in thin sheets. A variety of different plastic scintillators are available, with emission in red, blue and green. Other examples of scintillator material that may be used include and are not limited to Calcium Tungstate $CaWO_4$, with emission in the blue range of the spectrum at 400 nm.

With reference to FIGS. 4, 5, in an embodiment, one could implement a dual-energy flat-panel detector system 400/500, using $CaWO_4$ screen material for top scintillator layer 408/512, emitting in blue, and measuring predominantly the lower-energy X-rays. CsI(Tl) may be used for intermediate scintillator layer 406/508, emitting mostly in green, and measuring predominantly the higher-energy X-rays. In the embodiment, color filter 404/506 may consist of blue-transmitting and green-transmitting parts.

In another embodiment, top scintillator layer 408/512 may be made of Europium-doped GdOS, emitting in red, and measuring predominantly the lower-energy X-rays. Intermediate scintillator layer 406/508 may be made using CsI(Na), emitting mostly in blue, and measuring predominantly the higher-energy X-rays. In the embodiment, color filter 404/506 may consist of red-transmitting and blue-transmitting parts.

In another embodiment, top scintillator layer 408/512 may be made of Europium-doped GdOS, emitting in red, and measuring predominantly the lower-energy X-rays. Intermediate scintillator layer 406/508 may be made using CsI(Tl), emitting mostly in green, and measuring predominantly the higher-energy X-rays. In the embodiment, color filter 404/506 may consist of red-transmitting and green-transmitting parts.

Figure 7:
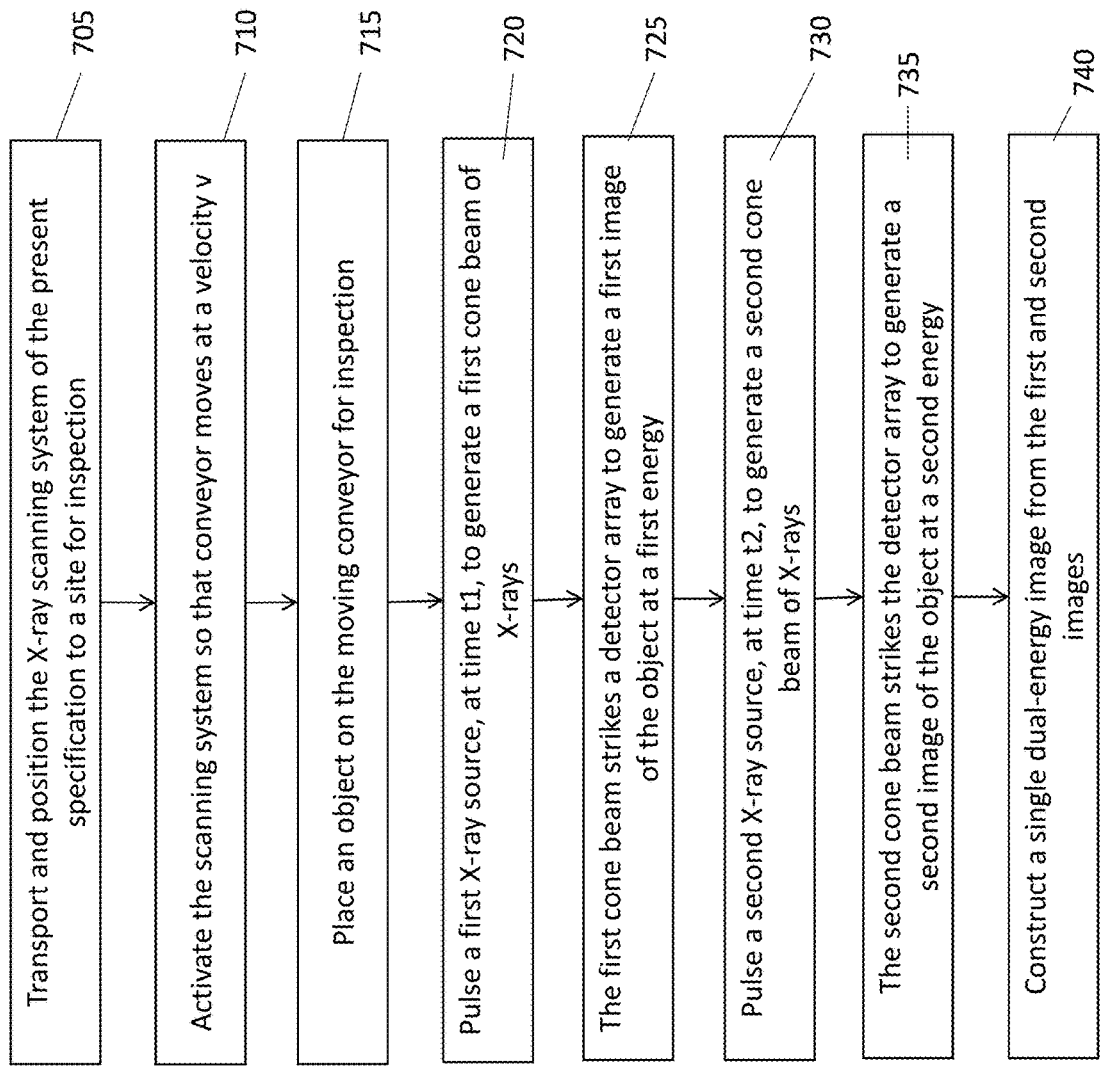
FIG. 7 is a flowchart illustrating a plurality of steps of a method of operating the X-ray inspection system of FIG. 1, in accordance with embodiments of the present specification; and, FIG. 8 illustrates a single beam dual-energy X-ray production system, in accordance with an embodiment of the present specification.

FIG. 7 is a flowchart illustrating a plurality of steps of a method of operating a portable and light-weight X-ray scanning system, in accordance with embodiments of the present specification. At step 705 the portable X-ray scanning system, such as system 100 of FIG. 1, is transported to and placed at a site for inspection, and connected to a source of power, which may either be wall-power, or produced by a generator, or produced by a battery. Optionally, an inverter may be used in combination with a battery in order to produce an alternating current power source. The system 100 may include a power switch to turn on primary power to all the subsystems. Referring now to FIGS. 1 and 7 simultaneously, at step 710 the system 100 is activated using the interface 112 so that the conveyor 108 starts moving with a predefined velocity v. At step 715, an object (such as a bag) for inspection is placed on the conveyor 108 to move the object through the inspection tunnel 106.

In accordance with embodiments, an X-ray source is a dual-energy pulsed X-ray source comprising two single-energy pulsed X-ray sources, such as the X-ray production system 300 described with reference to FIG. 3. Also, in accordance with embodiments, the 2D detector array 104 is a large-area dual-energy flat panel detector system, such as detector system 400 or 500 of FIG. 4 or 5 respectively. In alternate embodiments, the X-ray source is a continuous single-energy source while the detector array is a dual-energy detector system. In still alternate embodiments, the X-ray source is a dual-energy source while the detector array is a single-energy detector system. As the object moves through the tunnel 106, at step 720 a first X-ray source is pulsed at time t1 to produce a first beam of electrons accelerated over a first voltage V1. The first beam of electrons strikes a first angled surface or side of a target to generate a first cone beam of X-rays. At step 725, the first cone beam strikes the detector array to generate a first image of the object at a first energy corresponding to the first voltage V1.

At step 730, a second X-ray source is pulsed at time t2 (wherein t2>t1) to produce a second beam of electrons accelerated over a second voltage V2, different from the first voltage V1. The second beam of electrons strikes a second angled surface or side of the target to generate a second cone beam of X-rays. At step 735, the second cone beam strikes the detector array to generate a second image of the object at a second energy corresponding to the second voltage V2.

In embodiments V2>V1, therefore the first cone beam of X-rays is at a lower energy compared to the second cone beam. Each of the first and second cone beams of X-rays comprises a spectrum of X-ray energies, the first cone beam having more low-energy X-rays and the second cone beam having comparatively more high-energy X-rays. Accordingly, with reference to the detector system 400 of FIG. 4 for example, the thin top scintillator layer 408 predominantly measures low-energy X-rays while the thicker intermediate layer 406 predominantly measures high-energy X-rays.

In some embodiments, the target is configured and positioned as an inverted trapezoid such that the first and second angled sides of the trapezoid respectively face towards the first and second X-ray sources, the parallel sides of the trapezoid are substantially parallel to the direction of the first and second beams of electrons, and the shorter of the two parallel sides is placed downwards. However, in alternate embodiments the target can be of any polygonal shape as long as it includes the first and second angled sides that are inclined at an angle with reference to a plane of the detectors. The angle of inclination of the first and second opposing sides with reference to the plane of the detectors enable generation of the first and second cone beams such that apexes of the first and second cone beams are separated by a predefined distance d. Accordingly, the velocity v of the conveyor is determined to be v=d/(t2−t1) at step 710. This enables the first and second images to overlap. In alternate embodiments, the conveyor speed v is set for a desired throughput while the pulsation timing differential is determined as (t2−t1)=d/v to enable the first and second images to overlap.

Since the first and second images are aligned or overlap with each other, and since they were taken with first and second X-ray beams of different source voltages V1 and V2, a single dual-energy image may be constructed from the first and second images, at step 740.

The concept outlined through various embodiments of the present specification has several advantages. A major advantage is that it has very similar features to existing small baggage scanners used at checkpoints. Therefore, the concept of operation may be identical to that used for checkpoint screening. A bag is put on the conveyor belt at one end of the system, is transported through a tunnel to the other end, and an organic/inorganic color-coded image is displayed on the screen. Software may be used in embodiments of the present invention that is similar to the software used in current baggage scanner products, including existing operator-assist features.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A portable X-ray imaging system, comprising:
   a housing defining a tunnel for receiving an article to be inspected;
   a conveyor for conveying the article through the tunnel at a pre-defined speed;
   an X-ray production system positioned within said housing, comprising:
   a first X-ray source pulsed at a first time to generate a first electron beam along a first longitudinal axis, wherein said first X-ray source is positioned above the conveyor;
   a second X-ray source pulsed at a second time to generate a second electron beam along a second longitudinal axis, wherein the first and second X-ray sources are positioned opposing to each other, wherein the second time is different than the first time, and wherein said second X-ray source is positioned above the conveyor;
   a target positioned between the first and second X-ray sources, wherein the target has a first side facing the first X-ray source and a second side facing the second X-ray source, wherein the first electron beam strikes the first side at a first impact point to generate a first X-ray cone beam and the second electron beam strikes the second side at a second impact point to generate a second X-ray cone beam, and wherein respective apexes of the first and second X-ray cone beams are separated by a distance; and an X-ray detector system positioned within said housing and comprising at least one two-dimensional flat panel detector for generating a first image of the article corresponding to the first X-ray cone beam and a second image of the article corresponding to the second X-ray cone beam, wherein the first and second sides of the target are inclined at an angle with respect to a top surface plane of said at least one detector and wherein the pre-defined speed of the conveyor is a function of at least the first time and the second time.

2. The system of claim 1, wherein the first X-ray source is operated at a first voltage and the second X-ray source is operated at a second voltage, and wherein the second voltage is higher than the first voltage.

3. The system of claim 1, wherein an angle of inclination of the first side relative to the top surface plane of the at least one detector ranges from 10 to 45 degrees and wherein an angle of inclination of the second side relative to the top surface plane of the at least one detector ranges from 10 to 45 degrees.

4. The system of claim 1, wherein the first and second longitudinal axes are non-collinear and lie on a single plane.

5. The system of claim 1, wherein the first longitudinal axis lies at a first angle relative to the first side and the second longitudinal axis lies at a second angle relative to the second side, wherein said first and second angles are less than or equal to 10 degrees.

6. The system of claim 1, wherein the distance ranges from 1 cm to 5 cm.

7. The system of claim 1, wherein a difference between the first and second times is defined such that the first image overlaps the second image as the article is conveyed at the pre-defined speed.

8. The system of claim 1, wherein the two-dimensional flat panel detector has a first layer, a second layer of a first thickness positioned on top of said first layer, a third layer of a second thickness positioned on top of said second layer, and a fourth layer of a third thickness positioned on top of said third layer.

9. The system of claim 8, wherein a first additional layer is included between said first and second layers and a second additional layer is included between said third and fourth layers.

10. A portable X-ray imaging system, comprising:
a housing defining a tunnel for receiving an article to be inspected;
a conveyor for conveying the article through the tunnel at a pre-defined speed;
an X-ray production system positioned within said housing, comprising:
a first X-ray source pulsed at a first time to generate a first electron beam along a first longitudinal axis;
a second X-ray source pulsed at a second time to generate a second electron beam along a second longitudinal axis, wherein the first and second X-ray sources are positioned opposing to each other, and wherein the second time is greater than the first time;
a target positioned between the first and second X-ray sources, wherein the target has a first side facing the first X-ray source and a second side facing the second X-ray source, wherein the first electron beam strikes the first side at a first impact point to generate a first X-ray cone beam and the second electron beam strikes the second side at a second impact point to generate a second X-ray cone beam, and wherein respective apexes of the first and second X-ray cone beams are separated by a distance; and an X-ray detector system positioned within said housing and comprising at least one two-dimensional flat panel detector for generating a first image of the article corresponding to the first X-ray cone beam and a second image of the article corresponding to the second X-ray cone beam, wherein the first and second sides of the target are inclined at an angle with reference to a top surface plane of said at least one detector, wherein said at least one detector has a first layer, a second layer of a first thickness positioned on top of said first layer, a third layer of a second thickness positioned on top of said second layer, and a fourth layer of a third thickness positioned on top of said third layer and wherein the pre-defined speed of the conveyor is a function of the first time and the second time.

11. The system of claim 10, wherein said first layer comprises an amorphous silicon or CMOS detector substrate, said second layer comprises a color filter, said third layer comprises a first scintillator material that emits scintillation light in a first color, and said fourth layer comprises a second scintillator material that emits scintillation light in a second color.

12. The system of claim 10, wherein said first thickness is less than 1 mm but greater than 0 mm, said second thickness ranges from less than 1 mm to 3 mm, and said third thickness is less than 1 mm but greater than 0 mm.

13. The system of claim 10, wherein said first layer predominantly detects high energy X-rays while said fourth layer predominantly detects low energy X-rays.

14. The system of claim 10, wherein a first additional layer is included between said first and second layers and a second additional layer is included between said third and fourth layers.

15. The system of claim 14, wherein at least one of said first additional layer and second additional layer are fiber-optic plates.

16. The system of claim 14, wherein said second layer is deposited on said first additional layer, wherein said first additional layer comprises a fiber-optic plate.

17. The system of claim 14, wherein at least one of said first additional layer and second additional layer comprises a third scintillator material that emits scintillation light in a third color.

18. The system of claim 10, wherein a first additional layer is positioned below said second layer such that said second layer is adjacent to said first additional layer and wherein the first additional layer comprises a fiber-optic plate.

19. The system of claim 10, wherein said second layer is configured to permit two or more colors to penetrate there through.

20. The system of claim 10, wherein the first electron beam defines a first plane and the second electron beam defines a second plane and wherein the first plane and second plane are positioned proximate to each other within a range of 0 mm to 3 mm.

* * * * *